US006268202B1

(12) United States Patent
Huang et al.

(10) Patent No.: US 6,268,202 B1
(45) Date of Patent: *Jul. 31, 2001

(54) **STRAINS OF *CONIOTHYRIUM MINITANS* HAVING β-GLUCANASE ACTIVITY**

(75) Inventors: Hung Chang Huang, Lethbridge; Kuo Joan Cheng, Richmond; Jennifer L. Zantinge, Red Deer; Andre J. Laroche, Lethbridge, all of (CA)

(73) Assignee: Her Majesty the Queen in right of Canada as represented by the Department of Agriculture and Agri-Food Canada, Lethbridge (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/113,231

(22) Filed: Jul. 10, 1998

Related U.S. Application Data (60) Provisional application No. 60/052,278, filed on Jul. 11, 1997.

(51) Int. Cl.[7] ..................................................... C12N 1/18
(52) U.S. Cl. ........................ 435/254.1; 435/911; 424/93.5
(58) Field of Search ....................... 438/254.11; 424/911, 424/93.5

(56) References Cited

U.S. PATENT DOCUMENTS

| 4,395,490 | 7/1983 | Cooney et al. | 435/201 |
| 4,472,504 | 9/1984 | Gallo | 435/209 |
| 5,409,820 | 4/1995 | Gerson et al. | 435/125 |

FOREIGN PATENT DOCUMENTS

| 1950265 A1 | 1/1996 | (DE) . |
| WO 90/09436 | 8/1990 | (WO) . |

OTHER PUBLICATIONS

Huang et al., "Penetration of Hyphae of Sclerotinia sclerotiorum by Coniothyrium minitans Without the Formation of Appressoria," (1988) J. Phytopathology 123:133–39.

Tu et al., "Mycoparasitism by Coniothyrium minitans on Sclerotinia sclerotiorum sclerotiorum and its effect on Sclerotinia Germination," (1984) Phytopath.Z 109:261–268.

Jones, D., Gordon, A.H., and Bacon, J.S.D. 1974. Cooperative action by endo– and exo–beta– (1,3) –glucanases from parasitic fungi in the degradation of cell–wall glucans of Sclerotinia sclerotiorum. (Lib.) de Bary, Biochem. J. 140:47–55.

Jones, D. and Watson, D. 1969. Parasitism and lysis by soil fungi of Sclerotinia sclerotiorum (Lib.) de Bary, a Phytopathogenic Fungus. Nature 24:287–288.

Domsch, K.H., Gams, W., and Anderson, T.H. (eds.) 1980, Coniothyrium corda 1840 emend. Sacc. 1880 (nomen conservadum). In: Compendium of Soil Fungi. Academic Press, New York. vol. 1:228–231.

Sesan, T. and Baicu, T. 1993. New aspects of the biology of the hyperparasitic fungus Coniothyrium minitans Campbell. In: Revue Roumaine de Biologie. vol. 38 (No. 2) :132–137.

Huang, H.C. 1981. Distribution of Coniothyrium minitans in Manitoba sunflower fields. Can. J. Plant Pathol. 3:219–222.

Huang, H.C. and Hoes, J.A. 1976. Penetration and infection of Sclerotinia sclerotiorum by Coniothyrium minitans. Can. J. Bot. 54:406–410.

Huang, H.C. 1977. Importance of Coniothyrium minitans in survival of sclerotia of Sclerotinia sclerotiorum in wilted sunflower. Can. J. Bot. 55:289–295.

Huang, H.C. 1980. Control of sclerotinia wilt of sunflower by hyperparasites. Can. J. Plant Pathol. 2:26–32.

Huang, H.C. and Kokko, E.G. 1987. Ultrastructure of hyperparasitism of Coniothyrium minitans on sclerotia of Sclerotinia sclerotiorum. Can. J. Bot. 65:2483–2489.

Whipps, J.M. and Gerlagh, M. 1992. Biology of Coniothyrium minitans and its potential for use in disease biocontrol. Myco. Rs. 96 (II):897–907.

Rai, J. N., et al. 1978. Lysis of Sclerotia of Sclerotinia sclerotiorum and Its Possible Relation with Chitinase Activity. Indian J. Mycology and Plant Pathology. 8:103–107.

*Primary Examiner*—Irene Marx
(74) *Attorney, Agent, or Firm*—Greenlee, Winner and Sullivan P.C.

(57) ABSTRACT

Strains of the aerobic mycoparasitic fungus *Coniothyrium minitans* having high levels of β-glucanase activity have been obtained. Preferred strains have been deposited at the American Type Culture Collection under accession numbers 74415, 74416, 74417, 74418, 74419, 74435 and 74436. Methods for mutagenizing *C. minitans* 74415 and obtaining strains having β-glucanase activity are provided.

8 Claims, 1 Drawing Sheet

Figure 1

STRAINS OF *CONIOTHYRIUM MINITANS* HAVING β-GLUCANASE ACTIVITY

CROSS REFERENCE TO RELATED APPLICATIONS

This application claims priority from U.S. Provisional Patent Application Serial No. 60/052,278, filed Jul. 11, 1997, which is incorporated herein by reference in its entirety.

BACKGROUND OF THE INVENTION

1. Field of the Invention

The invention relates to strains of the aerobic mycoparasitic fungus *Coniothyrium minitans* having β-glucanase activity.

2. Description of the Related Art

A major factor affecting animal production is a efficiency of feed utilization. Efficient feed utilization requires efficient digestion of complex β-glucan substrates that are present in forage. β-glucans are one of the most abundant groups of naturally-occurring polysaccharides. β-glucans with (1,3), (1,4), (1,6) and (1,2) linkages have been identified in both bacteria and plants (Stone and Clark 1992), while (1,3) and (1,6) linkages are abundant in fungal cell walls (Wessels and Sietsma 1981). Fibre and β-glucans in feed are often poorly digested by animals, especially monogastric animals, resulting in waste. Diets containing certain forms of glucan (such as arabinoxylan in wheat and rye, or β-glucan in barley and oats) may also have deleterious effects on nutrient absorption and may promote intestinal disturbances by enteric pathogens.

The digestion of fibre and β-glucans in feed by livestock may be improved by enzyme supplementation (Shuttle 1995). Glycanolytic enzyme feed additives are thought to enhance fibre degradation and/or reduce viscosity in the gastrointestinal tract, thereby increasing feed intake and passage rate (Sears 1993). Currently, feed enzyme supplementation has been limited by the high cost of enzyme production. Industry relies on mass fermentation to produce feed enzymes and is limited to a small group of fungal (mainly Aspergillus, Penicillium and Trichoderma) and bacterial (*Bacillus coagulans, B. lichenformis, B. circulans* and *B. subtilis var.*) taxa as a source for these enzymes (Sears 1993). There is, therefore, an ongoing need for new microbial sources of β-glucan degrading enzymes (β-glucanases). Ideally, such microorganisms could be easily and inexpensively grown by liquid or solid state fermentation, and would have high levels of β-glucanase activity. Endo- and exo-1, 3-β-glucanase activity have been reported in the aerobic mycoparasitic fungus *Coniothyrium minitans* (Jones et al. 1973). However, the Jones et al. reference does not teach combined endo-1,3- and endo-1,4- β-glucanase activity of *C. minitans*. Combined endo-1,3- and endo-1,4-β-glucanase activity is the β-glucanase activity that is most useful for degrading β-glucans in animal feeds. Further, as the medium on which the *C. minitans* cultures of Jones et al. were grown consisted substantially of sclerotia of *Sclerotinia sclerotiorum*, a natural β-glucan source, the Jones et al. reference does not teach constitutive β-glucanase activity of *C. minitans* on a rich medium without a β-glucan source. Such a medium would be preferred for industrial fermentation applications. Teaching neither combined endo-1,3- and endo-1,4-β-glucanase activity nor constitutive β-glucanase activity of *C. minitans*, the Jones et al. reference does not suggest the utility of *C. minitans* as a useful source of β-glucanase enzymes.

SUMMARY OF THE INVENTION

The present invention provides biologically pure strains of the aerobic mycoparasitic fungus *Coniothyrium minitans* having high levels of β-glucanase activity when grown by liquid or solid state fermentation (*C. minitans* strains ATCC 74415, 74416 and 74417). Through mutagenesis of strain ATCC 74415, additional strains of *C. minitans* having high levels of β-glucanase activity have also been obtained (*C. minitans* strains ATCC 74418, 74419, 74435 and 74436).

A method for obtaining *C. minitans* strains having β-glucanase activity is also provided. Broadly stated, this method involves:

1. providing a plurality of cells of *Coniothyrium minitans* ATCC 74415;
2. exposing the cells to ultraviolet radiation to mutagenize the cells;
3. culturing the mutagenized cells on or in a culture medium to produce a plurality of cultures of *Coniothyrium minitans*;
4. testing the cultures of mutagenized cells for β-glucanase activity; and,
5. recovering from step (d) those cultures that have β-glucanase activity.

Solid or liquid culture media may be used. The culture medium used may be a minimal medium wherein the only carbohydrate source is a source of β-glucan. Such a medium will select for mutants having a mutation increasing β-glucanase activity and which can therefore utilize the β-glucan in the medium as a carbohydrate source and will therefore out-compete *C. minitans* cells which have a mutation down-regulating β-glucanase activity or no mutation. Alternatively, a rich medium containing sources of starch and simple sugars but no source of β-glucan can be used. Mutagenized *C. minitans* cells which still exhibit β-glucanase activity on the rich medium have constitutive β-glucanase activity, as no source of β-glucan is required to induce β-glucanase activity, and do not suffer β-glucanase activity repression due to the presence of starches and simple sugars. Starches and simple sugars are readily metabolized nutrient sources that would be ordinarily utilized before β-glucan, resulting in repression of β-glucanase activity.

Through UV mutagenesis, mutant strains of *C. minitans* having levels of β-glucanase activity on average 10 times higher than the parental source strain *C. minitans* ATCC 74415 have been obtained. These mutants (ATCC 74435 and 74436) possess constitutive β-glucanase activity which does not require induction by a source of a β-glucan substrate, and which is not repressed by the presence of carbohydrate sources such as starches or simple sugars. These characteristics make the *C. minitans* strains of the present invention excellent candidates for commercial β-glucanase production in that the high β-glucanase activity strains can be grown on an inexpensive solid medium such as waste potato peelings. Such a medium is high in simple sugars and starch and does not contain a source of β-glucan to act as an inducer. The solid growth medium can be inoculated with spores or mycelium of *C. minitans* strains of the present invention having high constitutive β-glucanase activity, and over the course of culture growth, the growth medium will be digested and replaced by a mass of *C. minitans* mycelia possessing β- glucanase activity. The β-glucanase activity can then be recovered by freeze-drying the mycelia and grinding it to a powder. Such culture conditions are much less expensive and easier to work with than liquid fermentation systems, particularly if specialized minimal media containing only β-glucan as a carbohydrate source were required to grow *C. minitans* strains which possess β-glucanase activity that requires the presence of a source of β-glucan as an inducer, and which is repressed by the presence of simple sugars or starches.

BRIEF DESCRIPTION OF THE DRAWINGS

The FIGURE is a dendogram of the genetic relatedness of C. minitans wild-type strains and mutants. This dendogram was made using only the combinations of primers yielding polymorphic fragments and fragments of differential intensity to maximize separation between the wild and mutant strains. The index of dissimilarity was generated with the unweighted pair-group method within the Numerical Taxonomy System Software ("NTSYS") (Exeter Software, Setauket, N.Y., USA).

DETAILED DESCRIPTION OF THE INVENTION

In order to provide a clear and consistent understanding of the specification and claims, including the scope to be given to such terms, the following definitions are provided.

A "biologically pure culture" of C. minitans, is a culture of C. minitans wherein all of the cells descend from a single spore or a singe hyphal tip, and are therefore substantially genetically identical.

A "β-glucanase" is an enzyme that is capable of hydrolyzing the polymeric substrate β-glucan. β-glucanases include, without limitation, endo-1,3-β-glucanases which hydrolyze β-1,3-linkages, endo-1,4-β-glucanases which hydrolyze β-1,4 linkages, and endo-1,3-1,4-β-glucanases which hydrolyze both β-1,3 an β-1,4 linkages. The following are enzymes classified as "β-glucanases" by the Nomenclature Committee of the International Union of Biochemistry and Molecular Biology ("IUBMB"), listed by the names recommended by the IUBMB and Enzyme commission ("EC") numbers:

Cellulase (EC 3.2.1.4)—Alternate names include endoglucanase, endo-1,4-β-glucanase, and carboxymethyl cellulase. Cellulase catalyses the endohydrolysis of 1,4-β-D-glucosidic linkages in cellulose. It will also hydrolyse 1,4-linkages in β-D-glucans also containing 1,3-linkages;

Endo-1,3(4)-β-glucanase (EC 3.2.1.6)—Alternate names include endo -1,4- β-glucanase, endo-1.3-β-glucanase, and laminarinase. Endo-1,3(4)-β-glucanase catalyses the endohydrolysis of 1,3- or 1,4-linkages in β-D-glucans when the glucose residue whose reducing group is involved in the linkage to be hydrolysed is itself substituted at C-3. Substrates include laminarin, lichenin and cereal d-glucans.

Glucan endo-1,3-β-D-glucosidase (EC 3.2.1.39)—Alternate names include 1->3)-β-glucan endohydrolase, endo-1,3-β-glucanase, and laminarinase. Glucan endo-1,3-β-D-glucosidase catalyses the hydrolysis of 1,3β-D-glucosidic linkages in 1,3-β-D-glucans, but has very limited action on mixed-link (1,3-1,4-)-β-D-glucans. Substrates include laminarin, paramylon and pachyman.

Glucan 1.3-β-glucanase (EC 3.2.1.58)—Alternate names include exo-1,3-β-glucanase, and exo-1,3-β-glucosidase. Glucan 1,3-β-glucosidase catalyses the successive hydrolysis of β-D-glucose units from the non-reducing ends of 1,3-β-D-glucans, releasing alpha-glucose. Glucan 1,3-β-glucosidase acts on oligosaccharides but very slowly on laminaribiose.

Glucan endo-1,2-β-glucosidase (EC 3.2.1.71)—Alternate names include endo-1,2-β-glucanase. Glucan endo-1,2-β-glucosidase catalyses the random hydrolysis of 1,2-glucosidic linkages in 1,2-β-D-glucans.

Licheninase (EC 3.2.1.73)—Alternate names include lichenase, β-glucanase, endo-β-1,3-1,4-glucanase, 1,3-1,4-β-D-glucan 4-glucanohydrolase, and mixed linkage β-glucanase. Licheninase catalyses the hydrolysis of 1,4-β-D-glycosidic linkages in β-D-glucans containing 1,3- and 1,4-bonds. Licheninase acts on lichenin (also known as "lichenan")and cereal β-D-glucans, but not on β-D-glucans containing only 1,3- or 1,4-bonds.

Glucan endo-1,6-β-glucosidase (EC 3.2.1.75) Alternate names include endo-1,6-β-glucanase. Glucan endo-1, 6-β-glucosidase catalyses the random hydrolysis of 1,6-linkages in 1,6β-D-glucans. Substrates include lutean, pustulan and 1,6-oligo-β-D-glucosides.

It is apparent from the foregoing, particularly from the alternate names provided, that the nomenclature used to identify β-glucanase-type enzymes has not been entirely consistent. This is due, in part, to early practices of naming these enzymes by the substrate hydrolyzed (eg. an enzyme that hyrolyzes laminarin becomes a laminarinase), which were later replaced by a practice of naming the enzyme according to the specific reaction catalyzed.

For the purposes of consistency and clarity, in the present specification and claims, β-glucanase enzyme activities are identified by the substrate hydrolyzed as exemplified in Example 1 herein. Hydrolysis of various polysaccharide substrates in Example 1 was measured by the liberation of reducing sugar (measured as glucose) during the incubation of various C. minitans fractions or samples with various polysaccharide substrates. Substrates on which C. minitans strains were tested for β-glucanase activity include, carboxymethylcellulose, lichenan, laminarin, and barley β-glucan. Hence, as used herein and in the claims:

"cellulos hydrolyzing activity" is β-glucanase activity of a strain of C. minitans that catalyzes the hydrolysis of cellulose to liberate reducing sugar (measured as glucose);

"lichenan hydrolyzing activity" is β-glucanase activity of a strain of C. minitans that catalyzes the hyrolysis of lichenan to liberate reducing sugar (measured as glucose);

"laminarin hydrolyzing activity" is β-glucanase activity of a strain of C. minitans that catalyzes the hydrolysis of laminarin to liberate reducing sugar (measured as glucose); and "barley β-glucan hydrolyzing activity" is β-glucanase activity of a strain of C. minitans that catalyzes the hydrolysis of barley β-glucan to liberate reducing sugar (measured as glucose).

The polysaccharide substrates mentioned above are readily available from commercial sources as follows:

Cellulos—available from Sigma-Aldrich Corporation, St. Louis, Mo. USA. as carboxymethylcellulose ("CMC") under Sigma Cat. No. C5013;

Lichenan—available from Sigma under sigma Cat. No. L6133, or from Megazyme International Ireland Limited, Bray Business Park, Bray, County Wicklow, Ireland, under Megazyme Cat No. P-LICHN;

Laminarin—available from Sigma under Sigma Cat. No. L9634; and

Barley β-glucan—available from Sigma under Cat. No. G6513,or from Megazyme under Cat Nos. P-BGBL, P-BGBM, and P-BGBH.

The CMC substrate consists only of 1,4-β-D-glucan. The laminarin substrate consists only of 1,3-β-D-glucan.

Lichenan and barley β-glucan consists of both 1,3- and 1,4β-D-glucan, though with different proportions of the two linkage types. Due to the composition of these substrates it is therefore known that a β-glucanase that hydrolyzes CMC to liberate reducing sugar must hydrolyze 1,4-linkages. Similarly, a β-glucanase that hydrolyzes laminarin to liberate reducing sugar must hydrolyze 1,3-linkages. β-glucanases that hydrolyze lichenan or barley β-glucan may hydrolyze 1,3- linkages, 1,4-linkages, or both. In the present invention, it is believed that the lichenan-hydrolyzing and barley β-glucan-hydrolyzing β-glucanases of the C. minitans strains of the present invention hydrolyze both 1,3- and 1,4- linkages, due to the high activity observed for these enzymes. Enzymes hydrolyzing only one of these linkages would be expected to have substantially lower activity. Also, the activity rates of the β-glucanases produced by the C. minitans strains of the invention clearly indicate that the β- glucanases have endo-β-glucanase activity (hydrolyzing internal glycosidic linkages within the polysaccharide chain) the rather than exo-β-glucanase activity (hydrolyzing glycosidic linkages of only the terminal monomers of the polysaccharide chain). Exo-β-glucanases would be expected to have substantially lower activity levels than those observed in the C. minitans strains of the invention.

A strain of C. minitans having "β-glucanase activity" is a strain of C. minitans which, under appropriate culture conditions, exhibits at least one of the above described β-glucan-hydrolyzing activities. Such β-glucanase activity may be recovered together with C. minitans mycelia, from the culture medium, or from a solvent used to extract the mycelia or the culture medium. β-glucanase activity can be quantified by various assays set forth in Example 1 herein, and which are there defined as the "Multi-well Plate Diffusion Assay", "OBR-HEC Assay", "Modified Reducing Sugar Assay", and "β-glucanase Plate Clearing Assay". Example 1 provides reproducible assay conditions for each of these assays that allow those skilled in the art to quantify the β-glucanase activity of cultures of *C. minitans.*

A strain of *C. minitans* having "constitutive " β-glucanase activity is a strain of *C. minitans* which exhibits β- glucanase activity when grown in a medium which is rich in simple sugars and starch, such as potato dextrose broth, and which does not contain a β-glucan source such as dried sclerotia of *Sclerotinia sclerotiorum.*

A "medium that includes assimilable sources of starch or sugars and is essentially free of assimilable sources of β-glucan" is a rich culture medium such as potato dextrose broth that is rich in starch and simple sugars, but which does not contain a β-glucan source, such as, for example, 1% dried sclerotia of *Sclerotinia sclerotiorum* or barley β-glucan.

A "medium that is essentially free of assimilable sources of starch or sugars and includes an assimilable source of β-glucan" is a minimal culture medium such as, for example, modified Czapek-Dox medium containing a β-glucan source such as, for example, 1% dried sclerotia of *Sclerotinia sclerotiorum.*

With respect to a *C. minitans* strain of the invention, a "mutant thereof having β-glucanase activity" is a *C. minitans* strain having β-glucanase activity which is derived from a *C. minitans* strain of the invention and which differs from that strain by a structural or compositional change in its DNA, whether as a result of normal segregation, a genetic recombination process, a spontaneous mutation, or a mutation induced by a mutagen, yet nevertheless retains β-glucanase activity.

A "unit of β-glucanase activity ("U")", including without limitation, carboxymethylcellulose hydrolyzing activity, lichenan hydrolyzing activity, barley β-glucan hydrolyzing activity, or laminarin hydrolyzing activity, is the amount of β-glucanase activity that causes the release of reducing sugars equivalent to 1 μmol of glucose per minute at 37° C., at pH 4.5.

*Coniothyrium minitans* strain 2134, a wild-type strain collected from the Canadian prairies, was found to exhibit high levels of β-glucanase activity when grown in liquid or solid state fermentation. The β-glucanases exhibited primarily laminarin hydrolyzing activity, with lower levels of carboxymethylcellulose hydrolyzing activity. *C. minitans* strain 2134 was deposited on Jun. 13, 1997 at the American Type Culture Collection ("ATCC"), 10801 University Boulevard, Manassas, Va., 20110-2209, USA) under accession number 74415. Colonies of *C. minitans* strain 2134 have golden-brown pigmentation, smooth edges, and are spore-producing (all phenotypic descriptions in this section are for fungal colonies grown on potato dextrose agar at room temperature (20–22° C.) under light for 14 days)

*C. minitans* strains 2130 and 2135, wild-type strains collected from the Canadian prairies, were also found to posses β-glucanase activity, including barley β-glucanase hydrolyzing activity, lichenan hydrolyzing activity, laminarin hydrolyzing activity, and cellulose hydrolyzing activity. Strain 2130 was deposited at the ATCC on Jun. 13, 1997 under accession number 74417. Colonies of *C. minitans* strain 2130 have olivaceous green pigmentation, smooth edges, and produce spores. Strain 2135 was deposited at the ATCC on Jun. 13, 1997 under accession number 74416. Colonies of *C. minitans* strain 2135 have olivaceous brown pigmentation, smooth edges, and produce spores.

Mutation of *C. minitans* strain 2134 was induced by ultra-violet irradiation. Several mutants exhibiting enhanced β-glucanase activity were isolated, and these were designated strains M11-3B2, A7-3D, A8-1and A10-4. Mutant strains M11-3B2, A8-1 and A10-4 were found to be relatively stable. Two constitutive mutants, strains A8-1 and A10-4, expressed barley β-glucan hydrolyzing activity in the absence of supplemental inducer (β-glucan substrate). Supernatants from A8-1 and A10-4 cultures grown in potato dextrose broth ("PDB") had maximum levels of β-glucanase activity on average 10 times greater than the parental strain. M11-3B2 had low levels of constitutive β-glucanase expression and enhanced laminarin hydrolyzing activity when grown in presence of β-glucan-rich substrate.

Strain M11-3B2 is a descendant of the original mutant M11 following 8 passages on 0.2% AZCL-β-glucan agar media. Strain M11-3 is a sister colony isolated from a single spore from the original M11 mutant and was deposited at the ATCC on Jun. 13, 1997 under accession number 74418. Colonies of *C. minitans* strain M11-3 have golden-brown pigmentation, smooth edges, and are spore forming. Colonies of *C. minitans* strain M11-3B2 have olivaceous golden-brown pigmentation, smooth edges, and are spore forming.

Strain A8-1 was deposited at the ATCC on Mar. 31, 1998 under accession number 74436. colonies of *C. Minitans* strain A8-1 have yellowish-white pigmentation, serrated edges, and produce very few spores. Strain A10-4 was deposited at the ATCC on Mar. 31, 1998 under accession number 74435. Colonies of *C. minitans* strain A10-4 have yellowish-white pigmentation, serrated edges, and produce very few spores.

*C. minitans* strain A7-3D was also found to possess β-glucanase activity, although this activity decreased over time. Strain A7-3D was deposited at the ATCC on Jun. 13, 1997 under accession number 74419. Colonies of strain A7-3D have golden-brown pigmentation, serrated edges, and produce spores.

Mutant *C. minitans* strains M11-3B2, A7-3D, A8-1and A10-4were obtained from *C. minitans* wild-type strain 2134 through mutagenesis by ultraviolet irradiation of *C. minitans* spore suspensions as described in Example 1 herein. In one approach, modified Czapek-Dox ("MCD") broth containing 0.2% barley β-glucan is used as a selective growth medium. MCD is a minimal medium that does not provide a carbohydrate source. β-glucan is added as the carbohydrate source (for example barley β-glucan). Strains of *C. minitans* having β-glucanase activity can utilize the barley β-glucan as a carbohydrate source. In this approach, mutated spore cultures having a mutation up-regulating β-glucanase activity will have higher β-glucanase activity and should therefore grow faster and out compete mycelia from spores with a mutation down-regulating β-glucanase activity of no mutation for β-glucanase activity. This approach does not, however, identify constitutive mutants which have β-glucanase activity in the absence of a source of β-glucan to act as an inducer. Moreover, the use of a minimal medium such as MCD does not differentiate between strains in which the β-glucanase activity is repressed by the presence of simple sugars such as glucose or other monosaccharides or disaccharides, or starches, and strains in which the β-glucanase activity is not repressed.

For large scale economic fermentation of *C. minitans* strains having β-glucanase activity, it is desirable to have constitutive β-glucanase activity that does not require induction by a source of β-glucan and which is not repressed by the presence of simple sugars. Although natural sources of β-glucan are available, such as the "inducer" described in the Examples herein which is a β-glucan source obtained from the sclerotia of the fungus *Sclerotinia sclerotiorum*, many inexpensive and readily available growth media, such as potato skins, do not provide a β-glucan source. It is preferable not to have to add a β-glucan source to the culture media.

In large scale fermentation, it is also preferable to use *C. minitans* strains having β-glucanase activity that is not repressed by the presence of simple sugars or starch for at least two reasons. First, it is preferable to be able to use an inexpensive medium such as potato skins which are rich in starch and simple sugars, rather than to use a non-naturally occurring minimal medium such as MCD. Second, even if a minimal medium such as MCD is used and β-glucan is provided as a carbohydrate source, the breakdown of the β-glucan by the β-glucanase activity of the *C. minitans* culture will result in the accumulation of simple sugars that would have to be removed to avoid repression of β-glucanase activity.

Therefore, in the preferred mutagenesis method, the mutagenized spores are cultured in a medium that does not provide a β-glucan source, and that is rich in simple sugars, such as PDB, to select mutants which possess constitutive β-glucanase activity that is not repressed by the presence of starch or simple sugars.

The use of the Multi-well Plate Diffusion Assay described in detail in Example 1 herein makes it possible to efficiently screen multiple cultures of *C. minitans* derived from mutagenized spores, whether the cultures are grown in 0.2% barley β-glucan MCD broth or PDB. The Multi-well Plate Diffusion Assay involves simultaneously contacting a plurality of samples taken from cultures of *C. minitans* derived from mutagenized spores against a solid assay medium so that each sample is in fluid communication with a portion of the surface of said solid assay medium and is in fluid isolation from every other sample. The solid assay medium contains an assay composition which, in the presence of β-glucanase activity in one of the *C. minitans* culture samples, releases a quantifiable market that diffuses into the sample in a quantity proportionate to the β-glucanase activity of the sample. Preferably the assay composition is a composition such as azurine cross-linked β-glucan ("AZCL-β-glucan") that is useful for detecting both endo-1,3-β-glucanase activity and endo-1,4-β-glucanase activity (as discussed above, the barley β-glucan substrate includes both 1,3- and 1,4- linkages, and β-glucanases that exhibit high barley β-glucan hydrolyzing activity are therefore expected to have both endo-1,3-β-glucanase activity and endo-1,4-β-glucanase activity. Degradation of the AZCL-β-glucan by endo-1,3-β-glucanase activity or endo-1,4-β-glucanase activity releases a quantifiable market, azurine blue dye. As the amount of AZCL-β-glucan degraded is proportionate to the level of β-glucanase activity in the sample. the amount of azurine blue dye released into the sample is proportionate to the β-glucanase activity of the sample.

Standard 96-well plates (or other multi-well plates) can be used both to culture samples of the mutagenized spore suspensions and to conduct the Multi-well Plate Diffusion Assay. A sample of each *C. minitans* culture grown in a first multi-well assay plate is transferred to a well in a second multi-well assay plate. The lid of the assay plate is lined with a solid agar assay medium that contains the AZCL-β-glucan assay composition. A layer of cheesecloth is placed on top of the assay medium to reinforce the assay medium and keep it intact during enzymatic digestion. The lid is placed on the plate so that the solid assay medium seals the top of each well, thereby isolating each well, and the plate with the lid in place is then carefully inverted. Incubation of the plate allows β-glucanase activity in the samples to break down the AZCL-β-glucan assay composition and release azurine blue dye into the sample, resulting in a visible blue color that can be quantified by measuring the optical density of the sample with an automatic plate reader. The greater the amount of azurine blue dye that diffuses into the sample, the greater the β-glucanase activity of the sample. Mutant *C. minitans* strains possessing high β-glucanase activity can then be further purified by sub-culturing single hyphal tips obtained from the growing mycelia, A preferred method for mutagenesis and isolation of strains of *C. minitans* having β-glucanase activity is performed as follows. *C. minitans* spore suspensions having a volume of about 10 ml and a density of about $1 \times 10^4$ spores/ml are provided and then exposed to ultraviolet light for a time sufficient to kill about 97–99% of the spares in the suspension. Samples of the irradiated spore suspension are then cultured in each well of a 96-well plate (or other multi-well plate) in an amount such that there are about 10–30 viable spores/well and screened for β-glucanase activity by an assay such as the Multi-well Plate Diffusion Assay described in Example 1 herein. The well having highest activity is plated on 0.2% AZCL-β-glucan MCD agar plates. Single hyphal tips from the colony grown on the 0.2% AZCL-β-glucan MCD agar plates are then picked and cultured on rich media such as potato dextrose agar ("PDA"). Mycelial plugs are removed from mutant cultures and cultured in MCD+1% sclerotia 'inducer' (β-glucan source) broth and then tested for β-glucanase activity by the Multi-well Plate Diffusion Assay. Single hyphal tips from the culture having the highest β-glucanase activity are subcultured on PDA/0.2% AZCL-β-glucan MCD agar and the culture stored in liquid nitrogen. The cultures are tested for β-glucanase activity by culturing mycelial plugs from the cultures in MCD+β-glucan-source broth and testing β-glucanase activity by the Multi-well Plate Diffusion Assay. The culture having the highest β-glucanase activity is stored in liquid nitrogen and scaled up in flasks. The β-glucanase activity of the scaled-up cultures is tested with the Modified Reducing Sugar Assay described in Example 1 herein. Samples of the scaled-up cultures are stored in liquid nitrogen. As discussed above, when this mutagenesis and isolation method is used to select strains of *C. minitans* having constitutive, non-repressed β-glucanase activity, the minimal medium MCD+β-glucan source is replaced with a rich medium such as PDB that is high in simple sugars and that does not contain a β-glucan source.

In an alternative approach discussed in Example 1 herein, cultures of *C. minitans* can be grown on solid media for exposure to a mutagen, and β-glucanase activity of the cultures subsequently tested directly on the solid media, by, for instance, an assay such as the β-glucanase Plate Clearing Assay described in Example 1.

Table 3 herein shows the combined endo-1,3-β-glucanase and endo-1.4-β-glucanase activity (barley β-glucan hydrolyzing activity) of constitutive mutants A10-4 and A8-1 versus that of the parental wild-type strain 2134 when grown on PDB (rich in simple sugars and starch, no source of β-glucan inducer). A unit of β-glucanase activity ("U") is defined as an amount of β-glucanase activity that causes the release of reducing sugars equivalent to 1 μmol of glucose per minute at 37° C. It is apparent in Table 3 that in triplicate tests, mutants A10-4 and A8-1 exhibited between 7.3 and 13.8 times the constitutive, non-repressed barley β-glucan hydrolyzing activity of the parental strain 2134 from which they were derived by the mutagenesis methods of the present invention. On average, mutants A10-4 and A8-1 exhibited about 10 times the constitutive, non-repressed barley β-glucan hydrolyzing activity of parental strain 2134. It is also apparent in Table 3 that 15 day PDB cultures of strains A10-4 and A8-1 had, respectively, greater than 2.0 U/ml and 2.5 U/ml barley β-glucan hydrolyzing activity as measured by the Multi-well Plate Diffusion Assay.

Table 4 summarizes additional superior properties of the *C. minitans* strains of the invention. Table 4 compares the intracellular carboxymethylcellulose hydrolyzing activity of *C. minitans* parental strain 2134 and mutants A8-1, A10-4 and M11-3B2. Various culture conditions were examined, including PDB (repression by simple sugars no source of β-glucan inducer). PDB+inducer (repression by simple sugars source of β-glucan inducer), and MCD+inducer (minimal medium with no source of repressing simple sugars, but with a source of β-glucan inducer). The results of principal interest are the results on PDB. As discussed previously, PDB is similar to the crude media that would preferably be used in a commercial fermentation setting. Strains that have β-glucanase activity on PDB have constitutive β-glucanase activity that is not repressed by the presence of simple sugars. As noted in column 3 of Table 4, although strain 2134 showed no carboxymethylcellulose hydrolyzing activity on PDB, each of mutants M11 3B2, A10-4 and A8-1 exhibited substantial carboxymethylcellulose hydrolyzing activity on PDB. It is also apparent in Table 4 that 15 day PDB cultures of strains A10-4 and A8-1 had greater than 0.4 U/ml and 0.7 U/ml cellulose hydrolyzing activity, respectively, when assayed by the OBR-HEC Assay. β-glucanase activity is shown in Table 4 as Units per ml of enzyme solution tested. That is, equal volumes of culture supernatant were assayed for each strain.

Barley β-glucan hydrolyzing activity, lichenan hydrolyzing activity, laminarin hydrolyzing activity and cellulose hydrolyzing activity of the *C. minitans* strains of the invention are shown in Table 5. The results summarized in Table 5 are for strains grown in MCD+1% sclerotia of *Sclerotinia scerotiorum* provided as an inducer (a natural β-glucan source), As such, these results are of particular interest with respect to mutant M11-3B2, which was selected on an MCD+inducer medium, and is less informative for mutants A8-1 and A10-4, which were selected on PDB, In a 15 day culture, mutant M11-3B2 showed 8% greater barley β-glucan hydrolyzing activity than parental strain 2134 and 46% greater lichenan hydrolyzing activity. That is, on average, more than 25% greater combined endo-1,3- and endo-1,4-β-glucanase activity than the parental non-mutagenized strain (2134). As discussed previously, as both barley β-glucan and lichenan are most effectively hydrolyzed by combined endo-1,3-β-glucanase activity and endo-1,4-β-glucanase activity, these results are indicative of increased combined endo-1,3-β-glucanase activity and endo-1,4-β-glucanase activity of the M11-3B2 mutant over the parental 2134 strain. As shown in Table 5, mutant M11-3B2 exhibited a broad range of β-glucanase activities, having greater than 7.0 U/ml laminarin hydrolyzing activity, 6.0 U/ml barley β-glucan hydrolyzing activity, 6.0 U/ml lichenan hydrolyzing activity, and 2.0 U/ml cellulose hydrolyzing activity when assayed by the Modified Reducing Sugar Assay, measured as a 15 day culture grown in MCD broth containing 1% sclerotia of *Sclerotinia scerotiorum*.

Table 5a shows the laminarin hydrolyzing ,activity, barley β-glucan hydrolyzing activity lichenan hydrolyzing activity and cellulose hydrolyzing activity of *C. minitans* strains 2130 and 2135 relative to strains 2134, 2132, and 2136, measured as nine day cultures grown in MCD broth containing 1% sclerotia of *Sclerotinia sclerotiorum*. Strains 2132 and 2136 are additional *C. minitans* strains collected from the Canadian prairies and deposited at the Lethbridge Research Centre Culture Collection. Though exhibiting lower β-glucanase activity than strain 2134 on each of the substrates tested, strains 2130 and 2135 had consistently strong β-glucanase activity on each of the four substrates.

Figure 1:
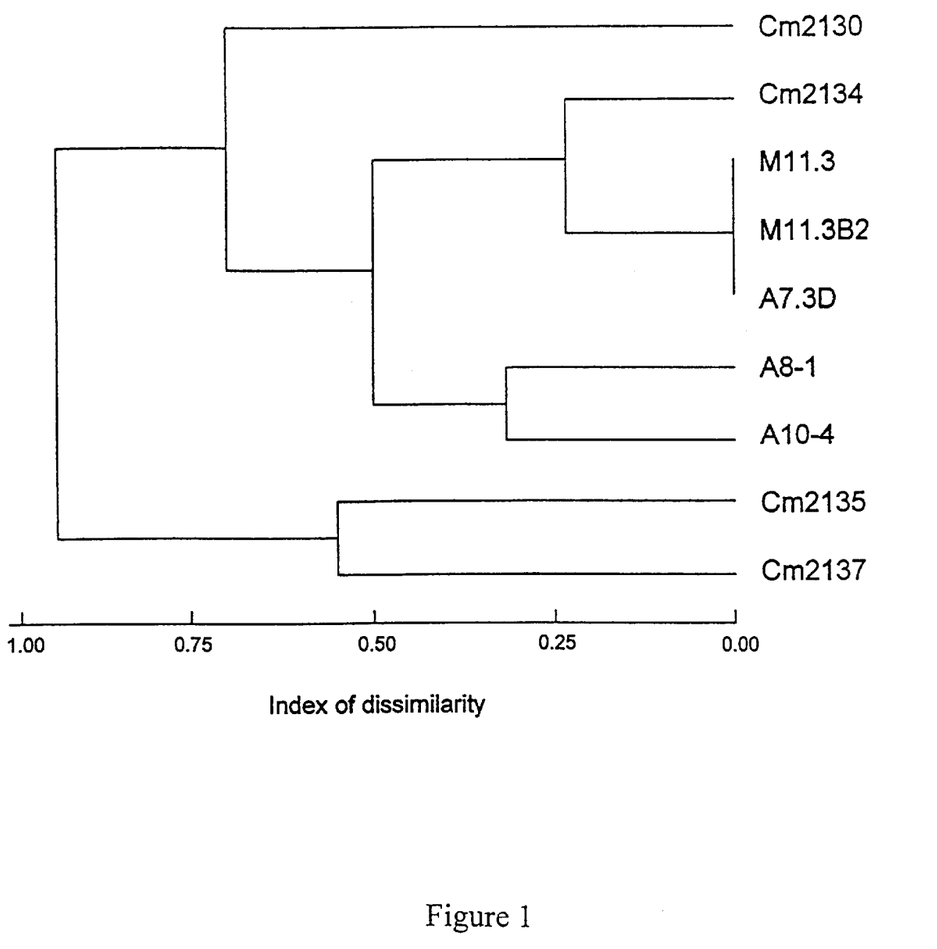

The amplified fragment length polymorphism ("AFLP") analysis described in Example 2 herein determined that wild-type strain 2134 and mutants M11-3, M11-3B2, A7-3D, A8-1 and A10-4 (obtained by mutagenesis) were clustered in a close group with an index of dissimilarity less than 0.50, indicating their high level of genetic relatedness, despite the substantial increases in β-glucanase activity of some of these mutants, relative to the parental strain 2134. It is therefore apparent that mutant strains of *C. minitans* that are derived from *C. minitans* strain 2134 (ATCC 74415) may retain β-glucanase activity, though having discernible (by AFLP or other forms of analysis) structural or compositional genomic changes. Those skilled in the art will recognize that such mutant strains derived from *C. minitans* ATCC 74415 can be readily tested for β-glucanase activity by the assays set forth in Example 1 herein, and -such strains which possess β-glucanase activity will be understood to fall within the scope and spirit of the present invention.

The invention is further illustrated by the following non-limiting examples.

EXAMPLE 1

β-glucanase Activity of *Coniothyrium minitans* Fungus and Culture Conditions

Strains of *Coniothyrium minitans* collected from Manitoba (Huang 1991) and Alberta, Canada, were deposited at the Lethbridge Research Centre type culture collection. The mutant strains M11-3B2, A10-4 and A8-1 were derived from the parental strain 2134 (wild type) after U.V. irradiation. The details of the mutagehesis scheme is described below. All stock cultures were stored in 10% flyxweol unswe liqued nitrogen. Working cultures were maintained on PDA (Difco Laboratories, Detroit, Mich., USQ) for short periods. Cultures on PDA were continuously screened for cultural variants by visible spontaneous mutations such as morphology or color. The methods of fungal characterization are described below in detail.

Production of Extracellular Enzymes in Shake Liquid Cultures

Extracellular β-glucanase activity was measured from *C. minitans* cultures supernatant grown in MCD+1% "inducer" broth medium containing the following (per liter of distilled water): $NH_4H_4H_2PO_4$, 2.0 g; $K_2HPO_4$, 1.0 g; $MgSO_4$, $7H_2O$, 0.5 g ; KCl, 0.5 g; $FeSO_4$, 0.01 g; "inducer" (dried powder of sclerotia of *Sclerotinia sclerotiorum* rich in β-*glucan*), 10.0 g; 1% $ZnSO_4$, 1 ml; 0.5% $CUSO_4$, 1 ml. Constitutive enzyme expression was measured in supernatant from *C. minitans* cultures grown in PDB (Difco). Cultures were grown at 20° C. under continuous light (12.5 $\mu$mole $m^{-2}s^{-1}$) and agitation (shaking at 200 rpm).

Dry Matter Weight of *C. minitans*

The solid maps from fungal cultures (45 ml after sampling) were collected at 15 days after growing in PDB, PDB+1% "inducer", and MCD+1% "inducer"and centrifuged at 5,000×g for 10 min. Mycelial pellets were transferred into aluminum foil measuring dishes and heated for 48 h at 90° C. The remaining dry mass in each plate was weighed.

Enzyme Assays

Extracellular enzyme activity of *C. minitans* was measured in sample supernatant using the following methods: 1) Multi-well Plate Diffusion Assay, 2) OBR-HEC Assay, 3) Modified Reducing Sugar Assay, and 4) β-glucanase Plate Clearing Assay. The Multi-well Plate Diffusion Assay, β-glucanase Plate Clearing Assay and OBR-HEC Assay were performed on supernatant from cultures grown in PDB. The β-glucanase Plate Clearing Assay can also be adapted to test for β-glucanase activity directly from growing cultures. Cultures grown in PDB could not be analyzed using the Modified Reducing Sugar Assay due to the resulting high background caused by the presence of large amounts of reduced sugars in the media. However, the OBR-HEC Assay can only test for endo-1,4-β-glucanase activity and the Multi-well Plate Diffusion Assay is limited by the availability of commercially prepared non-soluble AZCL substrates (Megazyme International Ireland Limited, Bray, County Wicklow, Ireland). The Modified Reducing Sugar Assay can be performed with any high quality substrate such as β-glucan, laminarin, lichenan or cellulose available from Sigma-Aldrich Corporation (St. Louis, Mo., USA).

Multi-well Plate Diffusion A-glucanase Assay

As used herein and in the claims, the β-glucanase assay described in this section shall be defined as the "Multi-well Plate Diffusion Assay".

In this assay and in each β-glucanase assay described subsequently herein, β-glucanase activity is reported as units of β-glucanase activity ("U") perml of *C. minitans* culture supernatant. As discussed previously, one unit of β-glucanase activity is defined as an amount of β-glucanase activity that causes the release of reducing sugars equivalent to 1 $\mu$mol of glucose per minute at 37° C.

For each β-glucanase activity assay described herein, fungal cultures for β-glucanase activity testing were grown in triplicate in 50 ml of broth in a 250 ml Erlenmeyer flask. Each flask was inoculated with 3 mycelium blocks (using a size 3 cork borer) taken from the edge of an actively growing colony (4–5 days old) on PDA. Cultures were incubated at 20° C. under continuous light (12.5 $\mu$mole $m^{-2}s^{-1}$) and on a shaker at 200 rpm. Fungal cultures were sampled at 3, 6, 9, 12, and 15 days after inoculation by removing 1 ml of growth media from each flask, Samples were collected in a 1.5 ml Eppendorf tubes and centrifuged at 5000×g for 5 min.

The assay medium used to screen high β-glucanase producing fungal isolates by the Multi-well Plate Diffusion Assay contained 0.2% AZCL-β-glucan and 2.0% agar dissolved in 25 mM sodium acetate, pH 4.5. The assay medium was autoclaved and cooled to 55° C. and stirred just prior to pouting to ensure the even distribution of AZCL-β-glucan particles. Exactly 20 ml of the assay medium was carefully pipetted into the lid of a 96 well plate on a level surface. Once solidified, a single layer of sterile cheese cloth cut to fit the 96 well plate was carefully place onto the assay medium, thereby lining the lid. The cheese cloth is added to reinforce the matrix assay medium, thereby strengthens the agar assay medium layer which tends to breakdown after enzyme digestion.

Fifty $\mu$l of each standard endoglucanase sample was added into the first row of wells (1*a*–*f*) in the 96-well diffusion assay plate and to the remaining walls, 50 $\mu$l of each test fungal culture supernatant was transferred from the 96-well mutagenesis plate to the corresponding well in the 96-well diffusion assay plate. All the wells in the diffusion assay plate were subsequently filled with 25 mM sodium acetate (pH 4.5) to a final volume of 350 $\mu$l. The lid lined with the assay medium was then care fully placed on top of the sample-filled 96-well assay plate and inverted while firmly pressing the lid and plate together. All air bubbles were removed by firmly pressing the bottom of the plate (forcing any air bubbles to rise to the inverted bottom of the well) to ensure direct contact was made between enzyme sample and the assay medium. Assay plates were incubated for several hours at room temperature (usually over night). To enhance the enzyme reaction rate, the assay plates could be incubated at a higher temperature (i.e. 37° C.–40°C.) thereby shortening the length of time required to perform the assay. The azurine cross-linked β-glucan, is insoluble in buffered solutions; however, rapid hydration of the substrate by the assay medium will form a soluble gel particle available for endoglucanase digestion. Digestion by endo-1,3-β-glucanase or endo 1,4-β-glucanase releases a blue dye fragment into the media, resulting in a visible blue color. Commercially available endoglucanases (either cellulase (EC 3.2.1.4), Megazyme with a measured specific activity on barley β-glucan, of 76.5 U/mg or licheninase (EC 3.2.1.73) with measured specific activity on barley β-glucan of 118 U/mg) were diluted in 25 Mm sodium acetate (pH 4.5) to a final concentration of 2, 1, 0.5, 0,25, 0.125, 0.06& 0.00 U/ml. Consequently, the blue dye osmotically diffuses from the solid agar assay medium and into the contacting sample/enzyme solution contained within the wells of 96-well plate. As a result, a more intense blue colour will develop in the sample well containing higher β-glucanase activity. To measure enzyme activity, the plates were carefully flipped upright and the lids were carefully removed. The absorbance of sample was read on an automatic plate reader at 590 nm. Sample activity was predicted from a standard curve produced from the relative optical densities of the standard endoglucanase samples in each individual plate. To minimize the diffusion of dye and enzyme between sample wells, the enzyme reaction incubation step was terminated by removing the lid, as soon as the blue colour became visible in the wells of the assay plate, Assays were performed in duplicate.

Ostazin Brilliant Red Hydroxyethylcellulose (OBR-HEC) Assay

As used herein and in the claims, the β-glucanase assay described in this section shall be defined as the "OBR-HEC Assay".

C. minitans cultures for β-glucanase activity testing were prepared as in the Multi-well Plate Diffusion β-glucanase Assay.

An 8 mg/ml solution of OBR-HEC (Sigma-Aldrich Cat. No. O-6879) substrate was prepared in 25 mM sodium accuracy, pH 4.5. The sample supernatant (enzyme solution) was diluted appropriately in 25 mM sodium acetate, pH 4.5. Substrate and enzyme solution were both equilibrated to 37° C. for 5 min. One hundred microliters of substrate was mixed with 100 μl of enzyme solution in a 1.5 ml Eppendorf micro-tube. Enzyme reactions were incubated for 120 min at 37° C. in a waterbath. Reactions were terminated by the addition of 0.8 ml of ice cold ethanol-acetone (2:1). The samples were mixed and allowed to stand for 30 min at room temperature. The samples were centrifuged for 2 min at 12,000×g in a microcentrifuge. The optical density of the supernatant was measured at 550 nm in a 0.5 ml cuvette. Each sample was measured in duplicate along with a background control. The controls were prepared as described above, but the substrate was added to the enzyme solution with the ethanol-acetone stop after the incubation. The sample test values were corrected by subtracting the background control values. Enzyme activities were estimated from a standard curve prepared using a commercially available cellulase (EC 3.2.1.4) (Megazyme) in an activity range of 0.1 to 1 U/ml.

Modified Reducing Sugar Assay

As used herein and in the claims, the β-glucanase assay described in this section shall be defined as the "Modified Reducing Sugar Assay".

C. minitans cultures for β-glucanase activity testing were prepared as in the Multi-well Plate Diffusion β-glucanase Assay.

Assays were performed in a 96-well titration plate. Fifty μl of sample supernatant/enzyme was added to each well and equilibrated to 37° C. Then 50 μl carboxymethylcellulose (#C-5013 Sigma-Aldrich Corporation, St. Louis, Mo., USA), lichenan (Sigma # L-6133), laminarin (Sigma, 9634) and β-glucan (Megazyme P-BGBH) diluted in 25 mM sodium acetate, pH 4.5, at a concentration of 5 mg/ml and equilibrated to 37°C. was added to the enzyme. Assays were allowed to react for 15 min at 37° C. and were stopped by the addition of 100 as of cold solution B (0.3% -dinitrophthalic acid) and solution C (1.8 M $K_2CO_3$+0.1 M $Na_2S_2O$, 1:1 v/v) mixed prior to use. Samples were heated for 45 Min at 95° C., until the reaction was completed. The absorbance was measured at an optical density of 410 nm using a plate reader. Background absorbance was measured by a control sample and subtracted from the sample absorbance. Control reactions were prepared for each sample, following the same method outlined above for the test assays without incubation; stop solutions B+C were added immediately following the addition of the substrate to the control samples. Enzyme activities were estimated from a standard curve, prepared from a series of glucose concentrations ranging from 50 βg/ml to 500 βg/ml Standards were prepared as described above for the test assays, except 100 μl of glucose standard was used in place of the 50 μl of substrate+50 μl of supernatant mixture. Samples which resulted in optical density greater than 3.0 were diluted and re-tested The samples were diluted as follows: day 3 not diluted, day 6 samples were diluted 1 in 2, day 9 and 12 samples were diluted 1 in 5, and day 15 samples were diluted 1 in 10. One unit of enzyme activity was defined as the amount of enzyme required to release reducing sugars equivalent to 1 μmol of glucose per min at 37° C.

β-glucanase Plate Clearing Assay

As used herein and in the claims, the β-glucanase assay described in this section shall be defined as the "β-glucanase Plate Clearing Assay".

C. minitans cultures for β-glucanase activity testing were prepared as in the Multi-well Plate Diffusion Assay.

C. minitans cultures can be screened directly on the AZCL-β-glucan MCD agar medium for β-glucanase activity. The AZCL-β-glucan MCD agar medium contained the following (per liter of distilled water): $NH_4H_2PO_4$, 2.0 g; $K_2HPO_4$, 1.0 g; $MgSO_4$, $7H_2O$, 0.5 g; KCl, 0.5 g; $FeSO_4$, 0.01 g: AZCL-β-glucan (Megazyme), 0.2 g; 1% $ZnSO_4$, 1 ml; 0.5% $CuSO_4$, 1 ml; and agar, 20.0 g. As AZCL-β-glucan particles are nonsoluble, it is important to cool media to 55° C. after autoclaving and stir just prior to pouring to ensure an even distribution of AZCL-β-glucan particles. β-glucanase activity on the 0.2% AZCL-β-glucan MCD agar medium was monitored by measuring the resulting zone of clearing surrounding the fungal colony caused by the hydrolysis of the insoluble AZCL-β-glucan particles and the release of a blue dye.

Supernatant from liquid cultures can also be analyzed for extracellular enzyme activity using this plate-clearing method, with a few adaptation to the method described above. To create wells, sterile stainless steel rings (1.0 cm diameter) were placed on top of 0.2% AZCL-β-glucan and 2% agar dissolved in 25 mM sodium acetate, pH 4.5 by autoclaving, A volume of 50 μl of test solution (enzyme) was placed into wells and allowed to diffuse into the media overnight (18 h). Once all the solution is absorbed into the media, the rings were removed. After 24 h incubation at 37° C. the diameter) of the zone of clearing was measured and recorded. A standard curve was prepared from the results of a commercially available endoglucanase (either cellulase (EC 3.2.1.4), Megazyme, with a measured specific activity on barley β-glucan, of 76.5 U/mg or licheninase (EC 3.2.1.73) with measured specific activity on barley β-glucan, of 118 U/mg) diluted in 25 mM sodium acetate (pH 4.5) to the final concentrations of 0.25,0.5,1.0,2.5 and 5 U/ml.

Phenotypic Characterization of C. minitans

C. minitans cultures were phenotypically characterized on 0.2% barley β-glucan MCD agar, 0.2% AZCL-β-glucan MCD agar, MCD+1% 'inducer' agar and on PDA. The barley β-glucan, MCD agar, 0.2% AZCL-β-glucan agar, and PDA were prepared as described above, MCD agar was prepared by adding an additional 20,0 g agar to 1 liter of MCD broth medium described above. Constitutive expression of β-glucanase was also screened on 0.2% AZCL-β-glucan supplemented PDA.

To characterize the C. minitans parental and mutant cultures phenotypically, a size 3 cork borer (6 mm in diameter) was used to cut agar plugs from mycelial mats from the edge of 4- to 5-day-old cultures on PDA. The mycelial plugs were inoculated on PDA, 0.2% barley β-glucan MCD agar, and 0.2% AZCL-β-glucan MCD agar with 1 plug at the center of each Petri plate. Cultures were incubated under light at 20° C. Phenotypic changes in colony colour, culture shape, growth-rate and sporulation were recorded 14 days after inoculation. Cultures were also washed with 75% ethanol for 15 min to extract colour from the fungal colonies (Huang, 1981).

Mutagenesis and Isolation of *C. minitans* Mutants

Method A: Ultraviolet (UV) irradiation of spores on agar

*C. minitans* spores from strain 2134 were streaked onto PDA and allowed to germinate for 48 h at 20° C. Germinated spores were then picked individually and transferred to AZCL-β-glucan MCD agar medium The germinated spores (9/Petri plate) were placed at a distance of 30 cm from a short wave (254 nm) ultraviolet germicidal lamp (model 782 L30, Westinghouse Electric Company, Pittsburgh, Pa., USA). With the Petri plate lids removed, the germinated spores were UV irradiated for 1 min, 2.5 min, or 5 min. One plate of germinated spores without exposure to UV was used as a control, After irradiation, the plates were placed in dark for 48 h at 20° C. and then placed under light at 20° C. After irradiation, fungal growth and β-glucanase expression was monitored daily. As the irradiated spores had been placed on AZCL-β-glucan MCD agar medium, β-glucanase activity could be directly monitored by the β-glucanase plate clearing assay method. Single hyphal tip cultures were obtained from those colonies which produced the greatest clearing zones surrounding the colony. High enzyme-producing cultures were repeatedly sub-cultured on minimal selective medium (MCD) supplemented with either 0.2% A7CL-β-glucan, 0.2% barley-β-glucan, or 0.2% 'inducer' as the only carbohydrate source. After a 5–7 day incubation at 20° C. under light, single hyphal tip cultures were established on PDA and 0.2% AZCL-β-glucan MCD agar from surviving irradiated spore cultures on the original 0.2% AZCL-β-glucan MCD agar plate initially exposed to UV.

Method B: Ultraviolet (UV) irradiation of spores in suspension

Spore suspensions (-10 ml, $1\times10^4$ spores/ml) were prepared in 0.2% barley β-glucan MCD broth containing the following (per liter of distilled water) $NH_4H_2PO_4$, b 2.0 g; $K_2HPO_4$, 1.0 g; $MgSO_4$, $7H_2O$, 0.5 g-, KCl, 0.5 g: $FeSO_4$, 0.01 g; barley β-glucan 0.2 g (Megazyme); 1% $ZnSO_4$, 1 ml; 0.5% $CuSO_4$, 1 ml. The spore suspension was placed in an open Petri dish at a distance of 10 cm from a short wave (254 nm) ultraviolet light germicidal lamp (Westinghouse 782 L30). A control sample (1 ml, was removed from the plate prior to UV exposure. Treated samples were removed after 1, 3, and 5 minutes of UV exposure. The length of UV exposure was adjusted to 3 min which killed approximately 97–99% of spores in the suspension, After irradiation, 200 μl of spore suspension was transferred into each well in a 96-well plate (or $1\times10^3$ irradiated spores/well or approximately 10–30 viable spores/well) The first lane was left as a control lane, which contained 200 μl of non-irradiated spores. Plates were placed at 20° C. in dark for the first 48 h to prevent photo reactivation and then transferred to full light at 20° C. for additional 14 days. To select constitutive mutants for β-glucanase activity, *C. minitans* spores were UV-irradiated as described above, except spores were suspended in PDB.

Primary Screening of High β-glucanase Producing *C. minitans*

The wells containing mutated *C. minitans* cultures with high β-glucanase activity were screened by the Multi-well Plate Diffusion Assay as described above. In a 96-well plate, 50 μl of cellulase enzyme standards at concentrations of 2, 1, 0.5, 0.25, 0.125, 0.06 & 0.00 U/ml (diluted in 25 mM sodium acetate, pH 4,5) were added into row 1 (wells 1*a*–*g*). Using an eight-channel micropipettor 50 μl from each well of the 96-well culture plates were aseptically transferred into the corresponding wells an the diffusion assay 96 well plates (note: the control lane 1, in the culture plate is not transferred to assay plate which is used for the enzyme standards).

The amount of mycelia present per well of the culture plate was estimated by reading the optical density at a wave length of 650 nm using the method described by Mohler et al. (1996). The wells with low mycelia amounts but high enzyme activity were targeted for isolation.

Isolation of Genetically Pure *C. minitans* Lines with Enhanced β-glucanase Activity Mycelium from the wells with the highest enzyme activity were transferred onto 0.2% AZCL-β-glucan MCD agar plates. After 3–4 days, single hyphal tips (~10/plate) were isolated from the colony, transferred onto PDA in Petri plates, and incubated at 20° C. under light for 4–5 days. Single hyphal tip cultures, which differed phenotypically were selected and tested for enzyme production. Mycelial plugs were removed from the edge of the mutant cultures on PDA using cork borer #3 and placed in 3 ml of MCD+1% 'inducer' broth medium in 15 ml test tubes with 3 plugs/tubes The test tubes were placed on an angle in a test tube rack on a shaker, and incubated a 20° C. while shaken at 200 rpm. At 7 and 14 days, cultures were tested for enzyme activity using the rapid diffusion plate assay described above. The highest β-glucanase producing *C. minitans* lines were stored in liquid nitrogen and single hyphal tips were sub-cultured and transferred to PDA/0.2% AZCL-β-glucan MCD agar. These mutant cultures twice isolated were regrown on PDA and retested for β-glucanase production in 3 ml or MCD+1% 'inducer' broth cultures as described above. After this double isolation step, the resulting fungal cultures with highest β-glucanase production were retested a third time for β-glucanase enzyme production. Fungal cultures were grown in larger 50 ml, flasks with 10 ml, of MCD+1% 'inducer' broth for 7 to 14 days and tested using the optimized reducing sugar assay. Enzyme production of mutants strains were compare to the enzyme activity of the parental strain.

Enzyme Analysis of *C. minitans* Mutants Derived From Mutagenesis and Isolation Methods A and B Extracellular enzyme production was measured from *C. minitans* parental strain 2134 and derived mutants, M11-3B2, A10-4 and A8-1. Cultures were grown in potato dextrose broth (PDB), PDB plus 1% 'inducer' (dried powder of sclerotia of *Sclerotinia scerotiorum*), and MCD+1% 'inducer' broth containing the following (per liter of distilled water):

$NH_4H_2PO_4$, 2.0 g; $K_2HPO_4$, 1.0 g; $MgSO_4$, $7H_2\mathbf{0}$, 0.5 g; KCl, 0.5 g; $FeSO_4$, 0.01 g; 'inducer', 10.0 g; 1% $ZnSO_4$, 1 ml; 0.5% $CuSO_4$, 1ml. PDA and PDB were prepared from commercially available media supplied by Difeo Laboratories (Detroit, Mich., USA). Fungal cultures were grown in triplicate in 50 ml of broth in a 250 ml Erlenmeyer flask. Each flask was inoculated with 3 mycelium blocks (using a size 3 cork borer) taken from the edge of an actively growing colony (4–5 days old) on PDA. Cultures were incubated at 20° C. under continuous light (12.5 μmole $m^{-2}s^{-1}$) and on a shaker at 200 rpm. Fungal cultures were sampled at 3, 6, 9, 12, and 15 days after inoculation by removing 1 ml of growth media from each flask. Samples were collected in a 1.5 ml Eppendorf tubes and centrifuged at 5000 x g for 5 min. Extracellular enzyme activity was measured in sample supernatant using the following methods: 1) the Multi-well Plate Diffusion Assay, 2) the OBR-HEC Assay, and 3) the Modified Reducing Sugar Assay. The Multi-well Plate Diffusion Assay and OBR-HEC Assay were performed on supernatant from cultures grown on PDB.

Zymogram—CMC

Cellulase (ccarboxymethylcellulose hydrolyzing activity) of parental *C. minitans* strain 2134 was investigated by zymogram analysis. Cellulase bands were detected by sodium dodecyl sulfate polyacrylamide gel electrophoresis ("SDS-PAGE") using Laemmli gels with 0.5% carboxymethylcellulose ("CMC") incorporated during the casting of the gels. The following samples were run on the gel: Lanes A, 20 µl supernatant; B, 20 µl concentrated supernatant (10X); C, low molecular weight marker; D, 20 µl concentrated supernatant (10X); E, 15 µl concentrated supernatant (10X); F, 20 µl supernatant; G, 20 µl concentrated supernatant (10X) from strain #2134. Following electrophoresis the gels were soaked in 1% Triton® X-100 for 1 h at room temperature (3 changes at 200 ml/wash) to remove SDS, 50 mM phosphate buffer (pH 6.5) for 1 h at 4° C. to renature the enzymes, and 50 mM phosphate buffer (pH 6.5) for 1–18 h at 37° C. for priming enzyme activity. Proteins were visualized by silver staining. The enzyme bands were visualized by staining the gels with 1% Congo red for 1 h and washing with 1 M NaCl. The gels were photographed using a green Wratten #58 filter (Eastman Kodak Company, Rochester, N.Y., USA) (f5.6 and 0.25 s exposure with Polaroid system and Polaroid 556 positive/negative film (Polaroid Corporation, Cambridge, Mass., USA)).

Results and Discussion

Mutagenesis and isolation of mutants

Method A. Ultraviolet (UV) irradiation of spores on agar

Approximately 88% of *C. minitans* spores remained viable after 1 min of UV irradiation, while 67% of spores remained viable after 2.5 min of irradiation and 50% of the spores remained viable after 5 min of irradiation. Approximately 50% of the viable irradiated fungal cultures had relatively large zones of clearing (>3 mm) when grown on 0.2% AZCL-β-glucan MCD agar medium for 7 days. Cultures with zones of clearing greater than 3 mm were further genetically purified by single hyphal tip isolations. Single pyphal tips were transferred to PDA and 0.2% AZCL β-glucan MCD agar. *C. minitans* mutants were also repeatedly sub-cultured on 0.2% AZCL β-glucan to force mutants to grow on β-glucan and assay for spontaneous upregulation in β-glucanase activity. Mutants were differentiated from the parental strain 2134 (wild-type) based on phenotypic changes such as colony colour, growth rate, sporulation, and shape when grown on PDA for 14 days under light.

Approximately 50 colonies of *C. minitans* mutants were obtained from the parental strain 2134 by the UV irradiation. These mutant isolates were subsequently cultured on 0.2% AZCL-β-glucan MCD agar media. In addition to phenotypic characterization, the mutants were tested for enzyme production. The *C. minitans* cultures were grown in 20 ml of MCD+1% 'inducer' broth in a 125 ml Erlenmeyer flask and assayed for extracellular enzyme activity at 3 and 5 days by the modified reducing sugar method. High β-glucanase producing mutants rapidly utilized the 'inducer' substrate which resulted in the clearing of the medium as early as 4–5 days after inoculation. The enzyme levels of two high β-glucanase producing mutants (M11 and M11-3, sistor cultures) were compared to the original parental 2134 wild-type. The M11 culture is a primary mutant produced by a 1 min exposure to UV irradiation followed by screening on 0.2% AZCL-β-glucan MCD agar media. M11-3 was isolated from a single spore from the original M11 mutant. The initial enzyme production experiment suggested that mutant M11-3 (1.88 U/ml) was about 5X higher than the parental strain 2134 (0.33 U/ml) for β-glucanase expression by 5 days of growth in MCD+1% 'inducer' broth. In an attempt to increase β-glucanase production by this mutant, it was continuously sub-cultured on 0.2% AZCL-β-glucan agar media. Mutant M11-3B2 is a descendant of the original mutant M11 following 8 passages on 0.2% AZCL-β-glucan agar media. Differences in morphological characteristics between mutant M11-3B2 and parental strain 2134 are evident in cultures grown on PDA for 14 days at 20° C. under light. The phenotypic characterization of these mutants is also summarized in Table 1. It was also found that mutant cultures derived from mutant M11 were unstable when grown on PDA as extended growth on PDA resulted in a decline in enzyme activity and, therefore, passage on a minimal restrictive media such as 0.2% AZCL-β-glucan MCD agar media appeared to be essential for culture maintenance.

Method B: Ultraviolet (UV) irradiation of spores in suspension

The strategy of using 0.2% β-glucan MCD broth as a selective growth medium for *C. minitans* was to restrict the growth of mycelia from spores with a mutation down-regulating β-glucanase production while selectively promoting growth of mycelia from spores with a mutation up-regulating β-glucanase activity. Under the assumption that mutated spore cultures with high β-glucanase activity would grow at a greater rate and produce more β-glucanase than mutated spore cultures with low β-glucanase production, the high β-glucanase-producing mutants would out-compete the low β-glucanase-producing mutants within the same well.

Approximately 6000 viable UV irradiated spores of *C. minitans* strain 2134 were screened by method B using 0.2% β-glucan MCD broth as the initial growth medium. Approximately 75 mutant cultures were isolated by single hyphal tip isolations from *C. minitans* cultures derived from wells with relatively high β-glucanase activities tested by the Multi-well Diffusion Plate Assay. These mutants were twice tested for β-glucanase production by growing in 3 ml of MCD+1% 'inducer' broth. Of these mutants, 26 mutants were re-tested a third time for enzyme production by growing cultures in a larger 10 ml volume of MCD+1% 'inducer' broth in a 50 ml Erlenmeyer. The highest enzyme-producing mutant appeared to be the mutant strain A7-3D. Phenotypical characteristics of 14-days-old culture of A7-3D grown on PDA under light are described in Table 1. However, as the A7-3D culture was further assayed for enzyme activity, it appeared to decline, and failed to out-produce the mutant M11-3.

The use of minimal restrictive medium 0.2% β-glucan MCD as a selective media does not differentiate between mutated spores exhibiting induced or constitutive β-glucanase production. Also, the 0.2% β-glucan MCD medium will not differentiate between mutated spores with β-glucanase production which are or are not repressed by the presence of simple sugars such as glucose. The use of PDB as a selective growth media would allow viable spores to grow regardless of an up or down-regulating mutation in β-glucanase production. PDB would provide an environment rich in simple sugars and therefore would normally repress β-glucanase expression in the parental strain 2134. PDB also would not induce β-glucanase expression as there would be very little β-glucan substrate in this medium to induce expression. Therefore, any wells containing mycelia which produces β-glucanases would suggest that the resulting mutation was constitutive or at least the fungal β-glucanase expression from the mycelia is partially unaffected by the presence of glucose and/or the lack of β-glucan.

The amount of mycelial growth per well was also thought to affect the amount of β-glucanase activity in the well. More mycelial growth correlated with the greater β-glucanase activity would not indicate increase β-glucanase expression.

Therefore, the optical density of 96 well culture plates were read at 650 nm in order to estimate mycelial growth. The optical density of mycelial cultures were visually confirmed under a dissecting microscope. Higher enzyme activity correlating with less mycelia suggest a mutation strongly up-regulating β-glucanase activity.

Approximately 4000 UV irradiated viable spores of *C. minitans* strain 2134 were grown in PDB and screened for β-glucanase activity. Of the 352 wells screened, two wells gave relatively high β-glucanase activity with relatively low amounts of mycelia present in the well. The mycelia from these wells were transferred and grown on PDA. Single hyphal tip isolations were made from the colony to establish pure cultures on PDA. The cultures derived from these two wells were grown on 3 ml PDB test tube cultures and screened for β-glucanase expression by the Multi-well Plate Diffusion Assay. Constitutively expressing β-glucanase cultures were identified by measuring β-glucanase activity in PDB. Strains A8-1 and A10-4 were identified as constitutive β-glucanase-producing mutants. Phenotypical characteristics of 14-days-old culture of A8-1 and A10-4 grown on PDA under light is described in Table 1.

Enzyme production by *C. minitans* mutants M11-3B2, A8-1 and A10-4 in liquid culture Growth of *C. minitans* strain 2134 and its mutants in liquid culture The growth of *C. minitans* in PDB. PDB+1% 'inducer', or MCD+1% 'inducer' broth was measured by dry mycelial mass after 15 days of growth per 50 ml culture. The average dry mycelial weight showed that each of the four strains of *C. minitans* grew the best in PDB+1% 'inducer', followed by PDB and then MCD+1% 'inducer' broth (Table 2). PDB is rich in nutrients (starches and simple sugars). The 1% 'inducer' is a natural source of carbohydrate, primarily consisting of β-glucan (Saito 1977). As expected, the cultures grew best in PDB+1% 'inducer' due to the greater amount of simple carbohydrate present. The parental strain 2134 grew faster in PDB than the mutant strains (Table 2) which correlates with the growth rate of strain 2134 on PDA (Table 1).

B-glucanase enzyme production by *C. minitans* strains 2134, M11-3B2, A8-1 and A10-4 grown in PDB The extracellular enzyme production by *C. minitans* parental strain 2134 and mutant strains M11-3B2, A8-1 and A10-4 when grown in PDB for 15 days was measured by the Multi-well Plate Diffusion Assay. The barley β-glucan hydrolyzing activity in the parental strain 2134 was greatly suppressed when grown in PDB, producing less than 0.25 U/ml of activity after 15 days of growth (Table 3). The barley β-glucan hydrolyzing activity of the mutants A10-4 and A8-1 was significantly higher in each of the triplicate experiments ranging from approximately 1.8–3.5 U/ml. Mutant A8-1 appeared to produce slightly higher barley β-glucan hydrolyzing activity than A10-4 (Table 3). The repression of barley β-glucan hydrolyzing activity in the parental 2134 vs mutants A10-4, A8-1 and M11-3B2 when grown on PDA supplemented with 0.2% AZCL-β-glucan is visible by zone of clearing surrounding the fungal colonies when grown on PDA supplemented with 0.2% AZCL-β-glucan. PDA is rich in starch and simple sugars which suppresses the expression of β-glucanases. The parental strain 2134 when grown on PDA supplemented with 0.2% AZCL-β-glucan, will not produce β-glucanase until after the starches and simple sugars have been utilized. Therefore, the mutant strains (A10-4, A8-1) with constitutive expression have a visible zone of clearing (approximately 5–7 mm wide) surrounding the fungal colony, whereas the parental and other mutant colonies with no constitutive expression do not have a zone of clearing. Mutant M11-3B2 also appeared to have some constitutive expression and had a smaller zone of clearing (approximately 3 mm wide).

Cellulose hydrolyzing activity of *C. minitans* parental 2134 and mutants, M11-3B2, A10-4 and A8-1

The OBR-HEC assay was used to measure extracellular cellulose hydrolyzing activity of *C. minitans* parental strain 2134, and of mutant strains M11-3B2, A8-1 and A10-4. The parental strain 2134 had insignificant amounts of cellulose hydrolyzing activity when grown in PDB while the mutant strains M11-3B2, A10-4 and A8-1 had varying levels of cellulose hydrolyzing activity (Table 4). A8-1 and A10-4 exhibited the highest levels of cellulose hydrolyzing activity, producing enzymes assayed at approximately 0.5–0.9 U/ml while M11-3B2 produced lower levels produced approximately 0.2 U/ml. When parental strain 2134 was grown in PDB with 1% inducer after a six to nine days of delay it began to slowly produce some cellulase, exhibiting approximately 0.2 U/ml cellulose hydrolyzing activity by 15 days (Table 4). Under the same conditions the mutant M11-3B2 produced approximately 2 U/ml of cellulose hydrolyzing activity by 15 days while mutant strains A8-1 and A10-4 by six days produced approximately 0.5 and 0.2 U/ml, respectively. When parental strain 2134 was grown in MCD+1% 'inducer' broth it had the highest cellulose hydrolyzing activity, approximately 3 U/ml by 15 days. The mutants A10-4 and A8-1 both had insignificant cellulose hydrolyzing activity while the mutant M11-3B2 had approximately 0.6 U/ml cellulose hydrolyzing activity when grown in MCD+1% 'inducer' broth (Table 4).

Endo-1,3-β-glucanase and endo-1,4-β-glucanase activities of *C. minitans* measured by modified reducing sugar assays Only the cultures grown in MCD+1% 'inducer' broth could be analyzed by the modified reducing sugar assay as cultures grown in PDB based media resulted in high reducing sugar background levels. The results of the modified reducing sugar assays are shown in Table 5, using laminarin (a), barley β-glucan (b), lichenan (c), and CMC (d), as substrates. The CMC substrate is made of only β-1,4-D-glucan. The laminarin substrate is made of only β-1,3-D-glucan. Lichenan and barley β-glucan consist of both 1,3- and 1,4-β-D-glucan. Parental strain 2134 produced the highest level of cellulose hydrolyzing activity (~3.4 U/ml) while mutant M11-3B2 produced the highest level of laminarin hydrolyzing activity (~7.2 U/ml) by 15 days. Also, M11-3B2 mutant strain produced more lichenan hydrolyzing activity (~6.5 U/ml) and similar amounts of barley β-glucan hydrolyzing activity (~6.5 U/ml) as the parental, 2134 (~4.5 U/ml and ~6.0 U/ml. respectively). The substrate lichenan has a higher ratio of β-1,3 to β-1,4 linkages than barley β-glucan, thereby explaining the slightly enhanced barley β-glucan hydrolyzing activity strain 2134. Mutants A10-4 and A8-1 produced insignificant amounts of cellulose hydrolyzing activity but produced slightly lower amounts of laminarin hydrolyzing activity (~4.3 U/ml and ~5.3 U/ml, respectively) than the parental strain 2134.

Zymogram—CMC

Zymogram analysis of cellulose hydrolyzing activity of *C. minitans* strain 2134 revealed a 66 kDa band with a very high cellulose hydrolyzing activity and two bands with less activity at 50 and 35 kDa which suggests several enzymes or enzyme subunits.

pH Optimum

The optimum pH for cellulose hydrolyzing activity of *C. minitans* strain A10-4 grown on PDB was determined to be 4.5.

The optimum pH for laminarin hydrolyzing activity of *C. minitans* strain 2134 grown on a minimal medium with a β-glucan source was determined to be 5.5.

Temperature Optimum

The optimum temperature for cellulose hydrolyzing activity activity of *C. minitans* strain A10-4 grown on PDB was determined to be 45° C.

EXAMPLE 2

DNA fingerprinting of *Coniothyrium minitans*, wild type strains and mutants

Four wild-type *Coniothyrium minitans* strains 2130, 2134, 2135, and 2137 and five mutant strains M11-3, M11-3B2, A7-3D, A8-1, and A10-4 originated from the wild-type strain 2134, were selected for DNA fingerprinting in this study. All *C. minitans* strains were collected from the Canadian prairies (Huang 1981) and deposited at the Lethbridge Research Centre type culture collection, where they have been maintained in secrecy, and have not been publicly disclosed. The original cultures of *C. minitans* strains and mutants were stored in 10% glycerol under liquid nitrogen, and the working cultures were maintained on PDA medium.

Three mycelia plugs of each *C. minitans* strains or mutants were inoculated into 50 ml of PDB liquid medium and incubated on a rotary shaker (200 rpm) under light at 20° C. Two weeks later, mycelia were collected by filtration, and freeze-dried until use. Genomic DNAs from the mycelium samples were isolated by using a modified proteinase K and phenol-chloroform procedure (Laroche et al. 1995). DNA concentrations in the extractions were measured by using a spectrophotometer (Beckman Coulter, Inc. Fullerton, Calif., USA, model DU-65) at 260 nm (50 $\mu$g/ml of DNA per O.D. unit). DNA size of each sample was verified in a 0.8% agarose gel with the ethidium bromide staining. Inoculation, incubation and DNA isolation from all 9 strains or mutants were repeated.

A modification of the original AFLP technique (Vos 1995) suitable for species with small genomes, such as most fungi, was applied for DNA fingerprinting of *C. minitans* strains and mutants. Total genomic DNAs (0.5 $\mu$g) was digested with 5 U Bg/II and 5 U Msel in 40 $\mu$l for 1 hour at 37° C. Then, 10 $\mu$l of a mixture containing 5 pmol Bg/II-adapter (Table 6), 50 pmol Msel-adapters (Table 6). 1 U T4 DNA ligase was added, and the restriction and ligation reaction was incubated at 37° C. for 3 hours.

The polymerase chain reaction ("PCR") amplification was performed in a touch-down procedure of 35 cycles with the following profile: 30 sec. for DNA denatured at 94° C., 1 min. for DNA annealing step, and 2 min. for DNA extension at 72° C. The annealing temperature in the first cycle was 65° C., then subsequently reduced 1° C. in each cycles for the next 10 cycles, finally continued at 56° C. for remaining 25 cycles. The reaction was conducted in a 20 $\mu$l mixture with 4 $\mu$l template DNA (1:10 diluted solution from restriction and ligation mixture), a pair of oligonucleotide primer (50 ng each), 0.5 U Taq DNA polymerase, 2 mM $MgCl_2$ and 2 mM dNTP in Tris-HCl buffer (pH8.3).

AFLP primers (Table 6) were designed and synthesized according to the sequences of the Bg/II-adapters and the MseI-adapters, also contained one or two additional, selective nucleotide at the 3' end of each primer. A total of 64 primer combinations were used in this study, including 4 MseI-primers ($P_{Mse}$A, $P_{Mse}$C, $P_{Mse}$G, and $P_{Mse}$T) and 16 Bg/II-primers ($P_{Bgl}$AA, $P_{Bgl}$AC, $P_{Bgl}$AG, $P_{Bgl}$At, $P_{Bgl}$CA, $P_{Bgl}$CC, $P_{Bgl}$CG, $P_{Bgl}$CT, $P_{Bgl}$GA, $P_{Bgl}$GC, $P_{Bgl}$GG, $P_{Bgl}$GT, $P_{Bgl}$TA, $P_{Bgl}$TC, $P_{Bgl}$TG, and $P_{Bgl}$TT). The primer combinations, which produced the polymorphic DNA banding patterns among the strains and/or mutants, were repeated at least twice for the AFLP marker verification.

The PCR-amplified products were first size-fractionated by electrophoresis on 2.0% agarose gels (TAE buffer, pH 8.0), and DNA bands were visualized by ethidium bromide staining. The products were also size-fractionated by polyacrylamide gel electrophoresis and visualized by silver staining. Aliquots (10 $\mu$l) of each PCR reaction were loaded onto a 7.0% polyacrylamide gel (29:1 ratio acrylamide:bisacrylamide) in 1X TBE buffer (50 mM Tris, 50 mM Boric acid, 1 mM EDTA, pH 8.0). Gels were run at constant voltage (100 V) and the Promega's DNA silver staining system (Promega Corporation, Madison, Wis., USA, Cat. No. DQ7050) was used for staining DNA fragments in the gels.

GeneScan® fluorometric measurement (Perkin Elmer Corporation, Foster City, Calif., USA) was further used for the measurement of molecular lengths and relative quantification of DNA fragments between *C. minitans* strains and mutants in this study. The 5 $\mu$M dUTP, labeled with 5-carboxyfluorescein fluorescent dye for the size detection, was randomly incorporated into DNA fragments during the PCR amplification. A volume of 0.5 $\mu$l ROX dye (GeneScan®-2500) was added into each loading sample as the internal lane size standard. The size-fractionated electrophoresis was conducted on an Applied Biosystems DNA Sequencer (Model 373A) with a GeneAmp Detection Gel (Perkin Elmer Corporation, Foster City, Calif., USA, Cat. No. F2252). GeneScan® 672 software (1993) was used to collect and analyse the data for DNA fragments detected in the electrophoresis.

Cluster analysis of AFLP markers for *C. minitans* strains and mutants was carried out by using the Numerical Taxonomy and Multivariate Analysis System (Rohlf 1992). According to the absence (0) or presence (1-3) of DNA amplified fragments, a pairwise of similarity matrix was conducted with Dist coefficients for the interval data from each strains and/or mutants. The corresponding cluster analysis was performed based on the sequential, agglomerative, hierarchical, and nested clustering methods, and the dendrogram of their genetic relatedness was generated with the unweighted pair-group method with arithmetic average linkage ("UPGMA") between clusters (Rohlf 1992).

Results and Discussion

Nine strains of *C. minitans* (four wild types and five mutants) were screened for AFLP markers by using synthetic oligonucleotide primers in a PCR amplification procedure. Although most primer combinations produced banding patterns that were easily scored, only a portion of amplified DNA fragments were clearly distinct and polymorphic (Table 8 and 9) which were used for DNA fingerprinting. In this study, of 64 primer combinations tested, 12 were determined to be informative and more than 160 DNA fragments were detected on agarose gels, in which only 19 distinct and polymorphic fragments were selected as AFLP markers (Table 7). The size fractionating of PCR amplified fragments produced similar DNA banding patterns between agarose gels stained with ethidium bromide and polyacrylamide gels stained with silver in this study (data not shown). Although agarose gels with ethidium bromide staining produced lower resolution, polymorphic DNA fragments could be clearly distinguished. Polyacrylamide gels with silver staining had higher resolution for DNA fragments ranging from 100 to 600 bp, however, it was difficult to detect the polymorphic fragments larger than 600 bp. GeneScan® was very sensitive to detect DNA polymorphisms among different samples, and the computer software also greatly improved the data analyses and result displays (Table 8 and 9).

Based on DNA banding patterns in agarose gels, the four *C. minitans* strains selected in this study were identified by using only the $P_{Mse}A$ and $P_{Bgl}CT$ primer combination (Tables 7 and 8). For example, with A/CT1 and A/CT2 markers, the four strains were initially divided into two groups: (1) strains 2130 and 2134; and (2) stains 2135 and 2137. From there, stains 2130 and 2134 can be further subdivided and identified by A/CT4 or A/CT5; and strains 2135 and 2137 can be further subdivided and identified by A/CT3 or A/CT4. It was also possible to discriminate these *C. minitans* strains by other AFLP primer combinations (Table 7).

In contrast to the four *C. minitans* strains, there were much fewer DNA polymorphisms among the five *C. minitans* mutants. In this study, of 64 primer combinations tested, no variation in the DNA banding patterns was observed among the three mutants M11-3, M11-3B2, and A7-3D. However, two AFLP markers, A/TA and G/CC, produced polymorphic DNA fragments which can discriminate A8-1 and A10-4 from the other three mutants (Tables 7 and 9). For example, low intensity of the 448 bp DNA fragment, amplified with the $P_{Mse}A$ and $P_{Bgl}TA$ primer combination, was scored for mutants M11-3, M11-3B2, and A7-3D while higher intensity was observed for mutant A8-1 and much stronger intensity was detected for mutant A10-4 (Table 9).

Cluster analysis of 19 AFLP markers for the nine *C. minitans* strains and mutants produced a dendrogram of genetic relatedness in good agreement with their putative pedigree (Figure). Three mutants (M11-3, M11-3B2, and A7-3D) were not differentiated in this dendrogram because no AFLP polymorphism had been detected among them. Strain 2134 and its five mutants were clustered in a close group with the index of dissimilarity (ID) less than 0.50, indicating their high level of genetic relatedness. For example, strain 2134 was clustered together with the three linked mutants (M11-3, M11-3B2, and A7-3D) with 0.23 ID, and the ID between A8-1 and A10-4 was only 0.32. However, four strains 2130, 2134, 2135 and 2137 had the IDs larger than 0.56, suggesting that their genotypes could have certain diversity. When all AFLP fragements were used for cluster analysis, all the nine *C. minitans* strains were clustered together and difficult to distinguish from each other, thus suggesting that *C. minitans* strains are highly related to each other.

Our results indicated that the AFLP technique is a powerful method for identification of *C. minitans* strains and mutants. AFLP markers detected in this study were reliable, repeatable, and unique for different *C. minitans* genotypes, thus very suitable for the DNA fingerprinting. Since all five mutants were derived from the parental strain 2134 and their genotypes could be almost identical, it was more difficult to distinguish different mutants than different strains at the DNA level. Theoretically, the AFLP fingerprinting technique can explore any polymorphism among different DNAs with the different primer combinations. Therefore, it should be possible to detect the unique DNA fingerprints for different mutants if more AFLP primer combinations are further examined.

TABLE 1

Phenotypic characterization of *Coniothyrium minitans*; wild type strains, 2130, 2134 and 2135 and mutant strains, M11-3, M11-3B2, A7-3D, AS-1 and A10-4.

| | colony characterization | | | |
|---|---|---|---|---|
| strains | growth[a] (cm) | pigment | edge | spores |
| 2130 (ATCC 74417) | 8.2 | olivaceous green | smooth | yes |
| 2134 (ATCC 74415) | 7.5 | golden brown | smooth | yes |
| 2135 (ATCC 74416) | 8.3 | olivaceous brown | smooth | yes |
| M11-3 (ATCC 74418) | 7.4 | golden brown | smooth | yes |
| M11-3B2 | 8.2 | olivaceous golden brown | smooth | yes |
| A7-3D (ATCC 74419) | 6.5 | golden brown | smooth | yes |
| A8-1 (ATCC 74436) | 7.2 | yellowish white | serrated | very little |
| A10-4 (ATCC 74435) | 6.8 | yellowish white | serrated | very little |

[a]average diameter of triplicate fungal colonies on PDA at room temperature under light for 14 days.

TABLE 2

Comparison of dry mycelia weight[z] of *C. minitans* strain 2134 (ATCC 74415), and mutant strains M11-3B2, A10-4 (ATCC 74435) and A8-1 (ATCC 74436) when grown in liquid culture on various growth media[x]

| growth | culture dry mycelia weight (grams) | | | |
|---|---|---|---|---|
| medium | 2134 | A8-1 | A10-4 | M11-3B2 |
| PDB | 0.62 | 0.43 | 0.45 | 0.54 |
| PDB + I | 0.65 | 0.70 | 0.80 | 0.87 |
| MCD + I | 0.42 | 0.46 | 0.48 | 0.50 |

[x]PDB (potato dextrose broth), PDB + I (potato dextrose broth + 1% 'inducer') or MCD + I (modified Czapek-Dox + 1% 'inducer').
[z]average dry mycelia weight from duplicate experiments.

TABLE 3

Constitutive extracellular barley β-glucan hydrolyzing activity (combined endo-1,3- and endo-1,4-β-glucanase activity) of *C. minitans* mutants, A10-4 and A8-1.

| | Units of β-glucanase | | |
|---|---|---|---|
| PDB[z] cultures | 2134 | activity[x] A10-4 | A8-1 |
| A | <0.25[a] | 1.82 | 2.11 |
| B | <0.25 | 2.42 | 2.65 |
| C | <0.25 | 2.41 | 3.45 |

[z]2134 (ATCC 74415) and mutant strains A10-4 (ATCC 74435) and A8-I (ATCC 74436) grown in PDB for 15 days. Cultures A, B, and C represent triplicate experiments grown on PDB.
[x]Enzyme activity was measured using the Multiwell Diffusion Plate Assay with AZCL-β-glucan as substrate.
[a]Enzyme activity expressed as Units per ml supernatant.

TABLE 4

Comparison of extracellular cellulose hydrolyzing activity (β-1,4-endoglucanase) activity of *C. minitans* parental strain, 2134 and mutants, A8-1, A10-4 and M11-3B2.

| strains | days | culture growth media* | | |
|---|---|---|---|---|
| | | PDB | PDB + I | MCD + I |
| A8-1 | 3 | 0 | 0 | 0 |
| | 6 | 0.24[a] | 0.48 | 0.35 |
| | 9 | 0.91 | 0.44 | 0 |
| | 12 | 0.60 | 0.29 | 0 |
| | 15 | 0.72 | 0.28 | 0.04 |
| A10-4 | 3 | 0 | 0 | 0 |
| | 6 | 0.9 | 0.18 | 0 |
| | 9 | 0.33 | 0.11 | 0 |
| | 12 | 0.46 | 0.13 | 0 |
| | 15 | 0.45 | 0.16 | 0.91 |
| M11-3B2 | 3 | 0 | 0 | 0 |
| | 6 | 0.14 | 0.29 | 0.76 |
| | 9 | 0.22 | 0.20 | 0.71 |
| | 12 | 0.18 | 0.27 | 0.97 |
| | 15 | 0.22 | 2.04 | 2.38 |
| 2134 | 3 | 0 | 0 | 0 |
| | 6 | 0 | 0 | 0.49 |
| | 9 | 0 | 0.11 | 1.04 |
| | 12 | 0 | 0.22 | 1.24 |
| | 15 | 0 | 0.21 | 3.35 |

*C. minitans strains were grown in either PDB, PDB + I % 'inducer' (PDB + I), or MCD + 1% 'inducer' (MCD + I) broth. Cellulose hydrolyzing activity is measured by the OBR-HEC Assay method for PDB and PDB + I, and by the Modified Reducing Sugar Assay for MCD + I. 'Inducer' is β-glucan rich substrate made of sclerotia of *Sclerotinia sclerotiorum*.
[a]Enzyme activity expressed as Units per ml supernatant.

TABLE 5

Comparison of β-glucanase activity of[z] *C. minitans* strains 2134, M11-3B2, A10-4 and A8-1 when grown in MCD + 1% 'inducer' broth.

| Strains | day | laminarin[a] | Barley β-glucan[b] | lichenan[c] | cellulose[d] |
|---|---|---|---|---|---|
| 2134 | 3 | 0 | 0.02[e] | 0 | 0 |
| | 6 | 0.57 | 2.05 | 0 | 0.49 |
| | 9 | 1.92 | 2.52 | 0.92 | 1.04 |
| | 12 | 4.69 | 5.58 | 2.08 | 1.24 |
| | 15 | 5.99 | 6.00 | 4.46 | 3.35 |
| M11-3B2 | 3 | 0.06 | 0.02 | 0 | 0 |
| | 6 | 1.02 | 3.31 | 0 | 0.70 |
| | 9 | 3.58 | 2.31 | 1.28 | 0.71 |
| | 12 | 5.71 | 4.49 | 2.65 | 0.97 |
| | 15 | 7.22 | 6.50 | 6.51 | 2.38 |
| A8-1 | 3 | 0.12 | 0.026 | 0 | 0 |
| | 6 | 1.84 | 2.97 | 0.03 | 0.35 |
| | 9 | 1.00 | 1.01 | 0.71 | 0 |
| | 12 | 2.64 | 2.72 | 1.61 | 0 |
| | 15 | 5.33 | 5.48 | 4.86 | 0.04 |
| A10-4 | 3 | 0.12 | 0.03 | 0 | 0 |
| | 6 | 0.69 | 0.37 | 0 | 0 |
| | 9 | 2.12 | 2.05 | 1.07 | 0 |
| | 12 | 3.95 | 3.20 | 3.00 | 0 |
| | 15 | 4.33 | 6.51 | 4.26 | 0.91 |

[z]Enzyme activities shown are the average of duplicate experiments. Enzyme activity of the supernatant from cultures was measured by the modified reducing sugar assay for activity on the following substrates:
[a]laminarin for laminarin hydrolyzing activity (endo-1,3-β-glucanase activity).
[b]barley β-glucan for barley β-glucanase activity (endo-1,3- and endo-1,4-β-glucanase activity).
[c]lichenan for lichenan hydrolyzing activity (endo-1,3- and endo-1,4-β-glucanase activity).
[d]cellulose for cellulose hydrolyzing activity (endo-1,4-β-glucanase activity).
[e]Enzyme activity expressed as Units per ml supernatant.

TABLE 5a

Comparison of β-glucanase activity[y] of *C. minitans* strains[z] 2130, 2132, 2134, 2135 and 2136 on various substrates when grown in MCD + 1% 'inducer' broth.

| | laminarin[a] | | barley β-glucan[b] | | lichenan[c] | | cellulose[d] | |
|---|---|---|---|---|---|---|---|---|
| Strains | avg | std | avg | std | avg | std | avg | std |
| 2130 | 3.25 | 0.75 | 2.11 | 0.17 | 2.40 | 0.49 | 1.23 | 0.33 |
| 2132 | 2.25 | 1.08 | 1.69 | 0.62 | 1.43 | 0.63 | 0.75 | 0.21 |
| 2134 | 5.85 | 1.62 | 4.13 | 1.93 | 1.66 | 0.21 | 1.41 | 0.45 |
| 2135 | 1.68 | 0.15 | 1.09 | 0.10 | 1.6 | 0.23 | 1.4 | 0.30 |
| 2136 | 1.17 | 0.62 | 0.88 | 0.08 | 0.55 | 0.30 | >0.1 | — |

[y]Enzyme activities are given as the average (avg) of triplicate experiments with their standard deviation (std) representing the maximum activity achieved by the culture within 11 days of growth. Enzyme activity is expressed as U/ml supernatant, measured by the Modified Reducing Sugar assay. All of the cultures reached their maximum enzyme activity after 9 days except for 2134, which continued to increase.
[z]All *C. minitans* strains are wild-type strains that were collected from the Canadian prairies and deposited at the Lethbridge Research Center type culture collection.
[a]laminarin for laminarin hydrolyzing activity (endo-1,3-β-glucanase activity)
[b]barley β-glucan for barley β-glucan hydrolyzing activity (endo-1-3-and endo-1-4-β-glucanase activity)
[c]lichenan for lichenan hydrolyzing activity (endo-1,3-and endo-1,4-β-glucanase activity)
[d]cellulose for cellulose hydrolyzing activity (endo-1,4-β-glucanase activity)

TABLE 6

DNA sequences of AFLP adapters and primers.[z]

```
BglII-adapter:  5' CTC GTG GAC TGC GTA C 3'      (SEQ ID NO: 1)
                3' CAC CTG ACG CAT GCT AG        (SEQ ID NO: 2)
             5'

MseI-adapter:   5' GAC GAT GAG TCC TGA G 3'      (SEQ ID NO: 3)
                3'    TA CTC AGG ACT CAT        (SEQ ID NO: 4)
             5'
```

TABLE 6-continued

DNA sequences of AFLP adapters and primers.[z]

BglII primers: 5' GGA CTG CGT ACG ATC TNN 3'  (SEQ ID NO: 5)

MseI primers:  5' GAT GAG TCC TGA GTA AN 3'   (SEQ ID NO: 6)

[z]Primers were designed and synthesized according to the sequences of adapters, the letter N at the 3' end of primers refers to one of four nucleolides: A ,C, G, and T.

TABLE 7

AFLP markers for *C. minitans* strains and mutants.[z]

| AFLP marker | Strains or Mutants | | | | | | | | |
|---|---|---|---|---|---|---|---|---|---|
| | 2130 | 2134 | 2135 | 2137 | M11-3 | M11-3B2 | A7-3D | A8-1 | A10-4 |
| A/AA | 0 | 1 | 0 | 1 | 1 | 1 | 1 | 1 | 1 |
| A/CC | 1 | 1 | 2 | 2 | 1 | 1 | 1 | 1 | 1 |
| A/CT1 | 1 | 1 | 2 | 2 | 1 | 1 | 1 | 1 | 1 |
| A/CT2 | 1 | 1 | 0 | 0 | 1 | 1 | 1 | 1 | 1 |
| A/CT3 | 0 | 0 | 2 | 1 | 0 | 0 | 0 | 0 | 0 |
| A/CT4 | 2 | 1 | 2 | 1 | 1 | 1 | 1 | 1 | 1 |
| A/CT5 | 0 | 1 | 0 | 0 | 1 | 1 | 1 | 1 | 1 |
| A/CT6 | 0 | 0 | 1 | 1 | 0 | 0 | 0 | 0 | 0 |
| A/CT7 | 1 | 0 | 1 | 1 | 0 | 0 | 0 | 0 | 0 |
| A/TA | 1 | 1 | 1 | 1 | 1 | 1 | 1 | 2 | 3 |
| C/CC1 | 1 | 1 | 1 | 0 | 1 | 1 | 1 | 1 | 1 |
| C/CC2 | 0 | 0 | 0 | 1 | 0 | 0 | 0 | 0 | 0 |
| C/CT | 1 | 1 | 1 | 2 | 1 | 1 | 1 | 1 | 1 |
| C/TC | 0 | 0 | 1 | 1 | 0 | 0 | 0 | 0 | 0 |
| C/TG | 1 | 0 | 1 | 1 | 0 | 0 | 0 | 0 | 0 |
| G/AA | 0 | 1 | 0 | 0 | 1 | 1 | 1 | 1 | 1 |
| G/AC | 0 | 0 | 0 | 0 | 1 | 1 | 1 | 1 | 1 |
| G/AG | 1 | 2 | 1 | 1 | 2 | 2 | 2 | 2 | 2 |
| G/CC | 0 | 0 | 0 | 0 | 0 | 0 | 0 | 1 | 2 |

[z]*C. minitans* strains 2130, 2134, 2135, and 2137 are wild types and strains M11-3, M11-3B2, A7-D, A8-1, and A10-4 are mutants originated from the parental strain 2134. AFLP markers were screened and detected based on agarose gels, and scored by the absence (0) and presence (1–3) of the selected amplified DNA fragments (1 = lower intensity fragment; 2 = higher intensity fragment; 3 = much stronger intensity fragment).

TABLE 8

DNA fingerprints of *C. minitans* wild (strains 2130, 2134, 2135 and 2137) with the AFLP primer combination A/CT. Molecular size for the different fragments were obtained from the GeneScan profiles.

| Strain | Peak | Minute | Size (bp) | Peak Height | Peak Area | Scan No. |
|---|---|---|---|---|---|---|
| 2130 | 17B (A/CT4) | 75 | 666 | 631 | 8551 | 754 |
| 2134 | 16B (A/CT5) | 80 | 717 | 1205 | 36993 | 802 |
| 2135 | 18B (A/CT4) | 75 | 665 | 513 | 7093 | 752 |
| 2135 | 27B (A/CT6) | 106 | 1019 | 521 | 8456 | 1060 |
| 2137 | 26B (A/CT6) | 106 | 1020 | 437 | 7715 | 1060 |

TABLE 9

DNA fingerprints of *C. Minitans* strain (2134) and its mutants (A8-1 and A10-4) with the AFLP primer combination A/TA. Molecular size for the different fragments were obtained from the GeneScan profiles.

| Strain or Mutants | Peak | Minute | Size (bp) | Peak Height | Peak Area | Scan No. |
|---|---|---|---|---|---|---|
| 2134 | 7B (A/TA) | 55 | 454 | 463 | 7992 | 555 |
| A8-1 | 7B (A/TA) | 54 | 449 | 1319 | 19605 | 548 |
| A10-4 | 8B (A/TA) | 54 | 448 | 3661 | 51308 | 548 |

LIST OF REFERENCES

GeneScan 672 software. 1993. User's Manual. Applied Biosystems, Perkin Elmer Corporation.

Huang, H. C. 1981. Distribution of *Coniothyrium minitans* in Manitoba sunflower seeds. Can. J. Plant Pathol. 3:219–222.

Jones, D., Gordon, A., and Bacon, J. 1973. Co-operative action by endo- and exo-β-(1-3)-glucanases from parasitic fungi in the degradation of cell-wall glucans of *Sclerotinia sclerotium* (Lib.) de Bary. Biochem. J. 140:47–55.

Laroche, A., D. A. Gauder, G. B. Schaalje, R. S. Erickson, and J. Ginns. 1995. Grouping and identification of low temperature basidiomycetes using mating, RAPD and RFLP analyses. Mycol. Res. 99(3):297–310.

Mohler, W. A. Charlton, C. A., and Blau, H. M. 1996. Spectrophotometric quantitation of tissue culture cell number in any medium. Biotechniques 21:260–266.

Rohlf, F. J. 1992. NTSYS-pc, Numerical Taxonomy and Multivariate Analysis System, Version 1.70. Exeter Software, Setauket, N.Y.

Saito, I. 1977. Studies on the maturation and germination of sclerotia of Sclerotinia sclerotiorum (Lib.) de Bary, a causal fungus of bean stem rot. Hokkaido Prefectural Central Agricultural Experiment Station, Naganuma, Hokkaido, Japan. Bulletin No. 26. 106 pp.

Sears, A. 1993. Industrial enzymes application: Using these concepts to match animal, enzyme and substrate in feed industry applications. Pp 372–395 in: Biotechnology in the Feed industry. Altech Technical Publications.

Shutte, J. B. 1995. Effects of β-glucanase (Allsym BG) supplement to a barley based diet on broiler chick performance. Pp 345–348 in: Biotechnology in the Feed industry. Altech Technical Publications.

Stone, B. A. and Clarke, A. E. 1992. Chemistry and Biology of (1-3)-β-glucans. La trobe University Press: Melbourne.

Vos, P., R. Hogers, M. Bleeker, et al. 1995. AFLP: a new technique for DNA fingerprinting. Nucleic Acids Research 23(21):4407–4414.

Wessels, J. G. H. and Seitsma. J. H. 1981. Fungal cell walls: A survey. pp. 352–394 In: Encyclopedia of Plant Physiology 13B (ed. W. Tanner & F. A. Loewus). Springer-Verlag: Berlin.

All publications mentioned in this specification are indicative of the level of skill in the art to which this invention pertains. All publications are herein incorporated by reference to the same extent as if each individual publication was specifically and individually indicated to be incorporated by reference.

Although the foregoing invention has been described in some detail by way of illustration and example, for purposes of clarity and understanding it will be understood that certain changes and modifications may be made without departing from the scope or spirit of the invention as defined by the following claims.

---

What is claimed is:

1. A biologically pure culture of a strain of *Coniothyrium minitans* having β-glucanase activity, wherein said strain of *Coniothyrium minitans* is:
   a. *Coniothyrium minitans* ATCC 74416, or a mutant thereof having β-glucanase activity;
   b. *Coniothyrium minitans* ATCC 74417, or a mutant thereof having β-glucanase activity;
   c. *Coniothyrium minitans* ATCC 74418, or a mutant thereof having β-glucanase activity;
   d. *Coniothyrium minitans* ATCC 74419, or a mutant thereof having β-glucanase activity;
   e. *Coniothyrium minitans* ATCC 74435, or a mutant thereof having β-glucanase activity; or,
   f. *Coniothyrium minitans* ATCC 74436, or a mutant thereof having β-glucanase activity.

2. A biologically pure culture of a strain of *Coniothyrium minitans* having β-glucanase activity as set forth in claim 1, wherein said strain of *Coniothyrium minitans* is *Coniothyrium minitans* ATCC 74415, or a mutant thereof having β-glucanase activity.

3. A biologically pure culture of a strain of *Coniothyrium minitans* having β-glucanase activity as set forth in claim 1, wherein said strain of *Coniothyrium minitans* is *Coniothyrium minitans* ATCC 74416, or a mutant thereof having β-glucanase activity.

4. A biologically pure culture of a strain of *Coniothyrium minitans* having β-glucanase activity as set forth in claim 1, wherein said strain of *Coniothyrium minitans* is *Coniothyrium minitans* ATCC 74417, or a mutant thereof having β-glucanase activity.

5. A biologically pure culture of a strain of *Coniothyrium minitans* having β-glucanase activity as set forth in claim 1, wherein said strain of *Coniothyrium minitans* is *Coniothyrium minitans* ATCC 74418, or a mutant thereof having β-glucanase activity.

6. A biologically pure culture of a strain of *Coniothyrium minitans* having β-glucanase activity as set forth in claim 1, wherein said strain of *Coniothyrium minitans* is *Coniothyrium minitans* ATCC 74419, or a mutant thereof having β glucanase activity.

7. A biologically pure culture of a strain of *Coniothyrium minitans* having β-glucanase activity as set forth in claim 1, wherein said strain of *Coniothyrium minitans* is *Coniothyrium minitans* ATCC 74435, or a mutant thereof having β-glucanase activity.

8. A biologically pure culture of a strain of *Coniothyrium minitans* having β-glucanase activity as set forth in claim 1, wherein said strain of *Coniothyrium minitans* is *Coniothyrium minitans* ATCC 74436, or a mutant thereof having β-glucanase activity.

* * * * *

SEQUENCE LISTING

```
<160> NUMBER OF SEQ ID NOS:  6

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: BglII -
      AFLP adapter

<400> SEQUENCE: 1
ctcgtggact gcgtac                                                      16

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence:BglII -
      AFLP reverse adapter

<400> SEQUENCE: 2
gatcgtacgc agtccac                                                     17

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence:MseI -
      AFLP adapter

<400> SEQUENCE: 3
gacgatgagt cctgag                                                      16

<210> SEQ ID NO 4
```

```
<211> LENGTH: 14
<212> TYPE: DNA
<213> ORGANISM: Artificial Sequence
<220> FEATURE:
<223> OTHER INFORMATION: Description of Artificial Sequence:MseI -
      AFLP reverse adapter

<400> SEQUENCE: 4
tactcaggac tcat                                                        14

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:BglII -
      AFLP primers
<221> NAME/KEY: misc_feature
<222> LOCATION: (17)..(18)
<223> OTHER INFORMATION: n is any one of a, c, g, or t

<400> SEQUENCE: 5
ggactgcgta cgatctnn                                                    18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:MseI -
      AFLP
      primers
<221> NAME/KEY: misc_feature
<222> LOCATION: (17)
<223> OTHER INFORMATION: n is any one of a, c, g, or t

<400> SEQUENCE: 6
gatgagtcct gagtaan                                                     17
```